United States Patent
Eckhouse et al.

(10) Patent No.: US 9,301,588 B2
(45) Date of Patent: Apr. 5, 2016

(54) HAIR REMOVAL APPARATUS FOR PERSONAL USE AND THE METHOD OF USING SAME

(71) Applicants: Shimon Eckhouse, Haifa (IL); Tuvia Dror Kutscher, Shoham (IL)

(72) Inventors: Shimon Eckhouse, Haifa (IL); Tuvia Dror Kutscher, Shoham (IL)

(73) Assignee: Syneron Medical LTD, Yokneam Illit (IL)

( * ) Notice: Subject to any disclaimer, the term of this patent is extended or adjusted under 35 U.S.C. 154(b) by 0 days.

(21) Appl. No.: 14/070,707

(22) Filed: Nov. 4, 2013

(65) Prior Publication Data

US 2014/0358132 A1 Dec. 4, 2014

Related U.S. Application Data

(62) Division of application No. 12/355,749, filed on Jan. 16, 2009, now Pat. No. 8,876,809.

(60) Provisional application No. 61/021,723, filed on Jan. 17, 2008, provisional application No. 61/045,282, filed on Apr. 16, 2008.

(51) Int. Cl.
*A45D 26/00* (2006.01)
*A61B 18/18* (2006.01)
(Continued)

(52) U.S. Cl.
CPC ............ *A45D 26/00* (2013.01); *A45D 26/0023* (2013.01); *A61B 1/06* (2013.01); *A61B 18/14* (2013.01); *A61B 18/18* (2013.01); *A61B 18/203* (2013.01); *B26B 19/42* (2013.01);
(Continued)

(58) Field of Classification Search
CPC ......... A45D 26/0023–26/0038; A61N 5/0617; B26B 19/3846; A61B 2018/00875
See application file for complete search history.

(56) References Cited

U.S. PATENT DOCUMENTS

| 1,430,354 A | 9/1922 | Burdick |
| 2,183,726 A | 2/1939 | Sommer et al. |

(Continued)

FOREIGN PATENT DOCUMENTS

| CN | 1078383 A | 11/1993 |
| EP | 0528055 A1 | 2/1993 |

(Continued)

OTHER PUBLICATIONS

PCT/IL08/01612 International Search Report.
(Continued)

*Primary Examiner* — Lynsey Crandall
*Assistant Examiner* — Nathan J Jenness
(74) *Attorney, Agent, or Firm* — Smith Tempel; Gregory Scott Smith

(57) ABSTRACT

Hair or partial hair removal system and hair growth deterrent that includes mechanical process for cutting, plucking or shaving hair follicles, along with pre and/or post skin treatment techniques. The skin treatment techniques can include the application of energy to the skin surface before, after and/or during the application of the mechanical process. Such techniques include the application of heat and/or energy from illumination sources and/or RF emitters. Further skin treatment techniques include the application of solutions before, after and/or during the mechanical process and/or the application of heat and/or energy. Overall, the system operates to treat an area of skin to facilitate the removal of all or a portion of hair, retard further growth, and recovery of skin surface.

2 Claims, 19 Drawing Sheets

(51) Int. Cl.
*A61B 18/20* (2006.01)
*B26B 19/42* (2006.01)
*B26B 19/46* (2006.01)
*B26B 21/48* (2006.01)
*A61B 1/06* (2006.01)
*A61B 18/00* (2006.01)
*A61B 18/14* (2006.01)

(52) U.S. Cl.
CPC .............. *B26B 19/46* (2013.01); *B26B 21/48* (2013.01); *A61B 2018/00029* (2013.01); *A61B 2018/00452* (2013.01); *A61B 2018/00476* (2013.01); *A61B 2018/00577* (2013.01); *A61B 2018/00875* (2013.01); *A61B 2018/1467* (2013.01); *A61B 2018/1807* (2013.01)

(56) References Cited

U.S. PATENT DOCUMENTS

| | | |
|---|---|---|
| 2,231,095 A | 2/1941 | Sommer et al. |
| 2,727,132 A | 12/1955 | Hills |
| 2,824,308 A | 2/1958 | Duncan |
| 2,888,927 A | 6/1959 | Fozard |
| 3,088,205 A * | 5/1963 | Ellis ............................ 30/34.05 |
| D196,532 S | 10/1963 | Facci |
| 4,016,886 A | 4/1977 | Doss et al. |
| 4,174,713 A | 11/1979 | Mehl |
| 4,182,329 A | 1/1980 | Smit et al. |
| 4,185,632 A | 1/1980 | Shaw |
| 4,200,104 A | 4/1980 | Harris |
| 4,211,230 A | 7/1980 | Woltosz |
| 4,321,926 A | 3/1982 | Roge |
| D269,294 S | 6/1983 | Rakocy et al. |
| D271,015 S | 10/1983 | Geraets |
| D271,199 S | 11/1983 | Geraets |
| 4,444,190 A | 4/1984 | Mutzhas |
| D274,462 S | 6/1984 | Rakocy et al. |
| 4,532,924 A | 8/1985 | Auth et al. |
| 4,550,728 A | 11/1985 | Runyon et al. |
| 4,553,936 A | 11/1985 | Wang |
| 4,566,454 A | 1/1986 | Mehl et al. |
| 4,630,182 A | 12/1986 | Moroi et al. |
| 4,686,986 A | 8/1987 | Fenyo et al. |
| 4,753,958 A | 6/1988 | Weinstein et al. |
| 4,784,135 A | 11/1988 | Blum et al. |
| 4,844,063 A | 7/1989 | Clark |
| 4,867,682 A | 9/1989 | Hammesfahr et al. |
| 4,869,584 A | 9/1989 | Dion |
| 4,940,456 A | 7/1990 | Sibalis et al. |
| 4,979,180 A | 12/1990 | Muncheryan |
| 5,016,999 A | 5/1991 | Williams |
| 5,071,418 A | 12/1991 | Rosenbaum |
| 5,087,240 A | 2/1992 | Sibalis |
| 5,125,928 A | 6/1992 | Parins et al. |
| 5,158,537 A | 10/1992 | Haak et al. |
| 5,169,384 A | 12/1992 | Bosniak et al. |
| 5,250,023 A | 10/1993 | Lee et al. |
| 5,286,479 A | 2/1994 | Garlich et al. |
| 5,316,473 A | 5/1994 | Hare |
| 5,348,554 A | 9/1994 | Imran et al. |
| 5,383,874 A | 1/1995 | Jackson et al. |
| 5,402,697 A | 4/1995 | Brooks |
| 5,406,340 A | 4/1995 | Hoff |
| 5,418,130 A | 5/1995 | Platz et al. |
| 5,487,662 A | 1/1996 | Kipke et al. |
| 5,509,916 A | 4/1996 | Taylor |
| 5,520,684 A | 5/1996 | Imran |
| 5,521,392 A | 5/1996 | Kennedy et al. |
| 5,564,851 A | 10/1996 | Connelly et al. |
| 5,582,476 A | 12/1996 | Hansen |
| 5,611,793 A | 3/1997 | Wilson et al. |
| 5,628,771 A | 5/1997 | Mizukawa et al. |
| 5,642,997 A | 7/1997 | Gregg et al. |
| 5,658,148 A | 8/1997 | Neuberger et al. |
| 5,674,191 A | 10/1997 | Edwards et al. |
| 5,681,282 A | 10/1997 | Eggers et al. |
| 5,683,380 A | 11/1997 | Eckhouse et al. |
| 5,693,052 A | 12/1997 | Weaver |
| 5,698,866 A | 12/1997 | Doiron et al. |
| 5,704,935 A | 1/1998 | Pahl et al. |
| 5,707,403 A | 1/1998 | Grove et al. |
| 5,718,702 A | 2/1998 | Edwards |
| 5,722,411 A | 3/1998 | Suzuki et al. |
| 5,735,844 A | 4/1998 | Anderson et al. |
| 5,755,753 A | 5/1998 | Knowlton |
| 5,769,880 A | 6/1998 | Truckai et al. |
| 5,776,092 A | 7/1998 | Farin et al. |
| 5,814,008 A | 9/1998 | Chen et al. |
| 5,824,023 A | 10/1998 | Anderson |
| 5,836,999 A | 11/1998 | Eckhouse et al. |
| 5,843,143 A | 12/1998 | Whitehurst |
| 5,846,252 A | 12/1998 | Mehl, Sr. |
| 5,868,744 A | 2/1999 | Willmen |
| 5,871,469 A | 2/1999 | Eggers et al. |
| 5,871,524 A | 2/1999 | Knowlton |
| 5,873,855 A | 2/1999 | Eggers et al. |
| 5,888,198 A | 3/1999 | Eggers et al. |
| 5,919,219 A | 7/1999 | Knowlton |
| 5,935,143 A | 8/1999 | Hood |
| 5,949,514 A | 9/1999 | Wargon |
| 5,954,710 A | 9/1999 | Paolini et al. |
| 5,961,482 A | 10/1999 | Chien et al. |
| 5,961,543 A | 10/1999 | Waldmann |
| 5,983,130 A | 11/1999 | Phipps et al. |
| 5,983,135 A | 11/1999 | Avrahami |
| 5,984,915 A | 11/1999 | Loeb et al. |
| 5,993,180 A | 11/1999 | Westerhof et al. |
| 6,024,733 A | 2/2000 | Eggers et al. |
| 6,030,384 A | 2/2000 | Nezhat |
| 6,042,959 A | 3/2000 | Debe et al. |
| 6,053,172 A | 4/2000 | Hovda et al. |
| 6,056,548 A | 5/2000 | Neuberger et al. |
| 6,063,108 A | 5/2000 | Salansky et al. |
| 6,066,134 A | 5/2000 | Eggers et al. |
| 6,078,830 A | 6/2000 | Levin et al. |
| 6,080,127 A | 6/2000 | Li et al. |
| 6,080,391 A | 6/2000 | Tsuchiya et al. |
| 6,081,934 A | 7/2000 | Stefanovsky et al. |
| 6,097,976 A | 8/2000 | Yang et al. |
| 6,107,326 A | 8/2000 | Jori |
| 6,132,701 A | 10/2000 | Perez et al. |
| 6,148,232 A | 11/2000 | Avrahami |
| 6,159,222 A | 12/2000 | Yiu |
| 6,173,202 B1 | 1/2001 | Eppstein et al. |
| 6,187,001 B1 | 2/2001 | Azar et al. |
| 6,190,609 B1 | 2/2001 | Chapman et al. |
| 6,191,110 B1 | 2/2001 | Jaynes et al. |
| 6,208,881 B1 | 3/2001 | Champeau |
| 6,210,402 B1 | 4/2001 | Olsen et al. |
| 6,221,095 B1 | 4/2001 | Van Zuylen et al. |
| 6,228,078 B1 | 5/2001 | Eggers et al. |
| 6,231,571 B1 | 5/2001 | Ellman et al. |
| 6,231,593 B1 | 5/2001 | Meserol |
| 6,251,127 B1 | 6/2001 | Biel |
| 6,256,525 B1 | 7/2001 | Yang et al. |
| 6,258,319 B1 | 7/2001 | Hearst et al. |
| 6,273,884 B1 | 8/2001 | Altshuler et al. |
| 6,275,728 B1 | 8/2001 | Venkatraman |
| 6,277,116 B1 | 8/2001 | Utely et al. |
| 6,280,438 B1 | 8/2001 | Eckhouse et al. |
| 6,288,498 B1 | 9/2001 | Cheng |
| 6,302,874 B1 | 10/2001 | Zhang et al. |
| 6,308,413 B1 | 10/2001 | Westerhof et al. |
| 6,309,387 B1 | 10/2001 | Eggers et al. |
| 6,325,797 B1 | 12/2001 | Stewart et al. |
| 6,343,400 B1 | 2/2002 | Massholder et al. |
| 6,343,933 B1 | 2/2002 | Montgomery et al. |
| 6,352,535 B1 | 3/2002 | Lewis et al. |
| 6,353,763 B1 | 3/2002 | George et al. |
| 6,374,653 B1 | 4/2002 | Gokcebay et al. |
| 6,400,976 B1 | 6/2002 | Champeau |
| 6,406,157 B1 | 6/2002 | Audet |
| 6,413,255 B1 | 7/2002 | Stern |

(56) References Cited

U.S. PATENT DOCUMENTS

| | | |
|---|---|---|
| 6,413,268 B1 | 7/2002 | Hartman |
| 6,419,674 B1 | 7/2002 | Bowser et al. |
| 6,425,912 B1 | 7/2002 | Knowlton |
| 6,433,343 B1 | 8/2002 | Cimino et al. |
| 6,440,121 B1 | 8/2002 | Weber et al. |
| 6,461,354 B1 | 10/2002 | Olsen et al. |
| 6,461,567 B1 | 10/2002 | Hearst et al. |
| 6,462,070 B1 | 10/2002 | Hasan et al. |
| 6,471,716 B1 | 10/2002 | Pecukonis |
| 6,477,410 B1 | 11/2002 | Henley et al. |
| 6,482,201 B1 | 11/2002 | Olsen et al. |
| 6,482,204 B1 | 11/2002 | Lax et al. |
| 6,487,447 B1 | 11/2002 | Weimann et al. |
| 6,490,482 B2 | 12/2002 | Mori et al. |
| 6,493,940 B2 | 12/2002 | Westerhof et al. |
| 6,494,900 B1 | 12/2002 | Salansky et al. |
| 6,497,702 B1 | 12/2002 | Bernaz |
| 6,508,813 B1 | 1/2003 | Altshuler |
| 6,510,341 B1 | 1/2003 | Kuribayashi et al. |
| 6,511,475 B1 | 1/2003 | Altshuler et al. |
| 6,514,243 B1 | 2/2003 | Eckhouse et al. |
| 6,514,248 B1 | 2/2003 | Eggers et al. |
| 6,517,532 B1 | 2/2003 | Altshuler et al. |
| 6,533,775 B1 | 3/2003 | Rizoiu |
| 6,544,259 B1 | 4/2003 | Tsaliovich |
| 6,544,261 B2 | 4/2003 | Ellsberry et al. |
| 6,558,653 B2 | 5/2003 | Andersen et al. |
| 6,572,637 B1 | 6/2003 | Yamazaki et al. |
| 6,582,429 B2 | 6/2003 | Krishnan et al. |
| 6,594,905 B2 | 7/2003 | Furst et al. |
| 6,595,947 B1 | 7/2003 | Mikszta et al. |
| 6,595,990 B1 | 7/2003 | Weinstein et al. |
| 6,597,946 B2 | 7/2003 | Avrahami et al. |
| 6,602,245 B1 | 8/2003 | Thiberg |
| 6,611,706 B2 | 8/2003 | Avrahami et al. |
| 6,611,707 B1 | 8/2003 | Prausnitz et al. |
| 6,612,819 B1 | 9/2003 | Furst et al. |
| 6,615,079 B1 | 9/2003 | Avrahami |
| 6,618,620 B1 | 9/2003 | Freundlich et al. |
| 6,620,158 B2 | 9/2003 | Ronci |
| 6,623,454 B1 | 9/2003 | Eggers et al. |
| 6,629,974 B2 | 10/2003 | Penny et al. |
| 6,632,002 B1 | 10/2003 | Chubb et al. |
| 6,632,193 B1 | 10/2003 | Davison et al. |
| 6,632,220 B1 | 10/2003 | Eggers et al. |
| 6,637,877 B1 | 10/2003 | Hartley et al. |
| 6,659,106 B1 | 12/2003 | Hovda et al. |
| 6,662,054 B2 | 12/2003 | Kreindel et al. |
| 6,663,620 B2 | 12/2003 | Altshuler et al. |
| 6,676,655 B2 | 1/2004 | McDaniel |
| 6,678,554 B1 | 1/2004 | Sun et al. |
| 6,702,808 B1 | 3/2004 | Kreindel |
| 6,708,060 B1 | 3/2004 | Avrahami et al. |
| 6,711,435 B2 | 3/2004 | Avrahami |
| 6,719,754 B2 | 4/2004 | Underwood et al. |
| 6,723,092 B2 | 4/2004 | Brown et al. |
| D490,156 S | 5/2004 | Fischer et al. |
| D490,526 S | 5/2004 | Jonsen |
| 6,740,079 B1 | 5/2004 | Eggers et al. |
| 6,743,211 B1 | 6/2004 | Prausnitz et al. |
| 6,758,845 B1 | 7/2004 | Weckwerth et al. |
| 6,761,729 B2 | 7/2004 | Babaev |
| 6,767,341 B2 | 7/2004 | Cho |
| 6,770,069 B1 | 8/2004 | Hobart et al. |
| 6,773,431 B2 | 8/2004 | Eggers et al. |
| 6,780,838 B2 | 8/2004 | Lipton et al. |
| 6,795,728 B2 | 9/2004 | Chornenky et al. |
| RE38,634 E | 10/2004 | Westerhof et al. |
| 6,887,260 B1 | 5/2005 | McDaniel |
| 6,889,090 B2 | 5/2005 | Kreindel |
| 6,905,496 B1 | 6/2005 | Ellman et al. |
| 6,918,907 B2 | 7/2005 | Kelly et al. |
| 6,974,450 B2 | 12/2005 | Weber et al. |
| 6,997,923 B2 | 2/2006 | Anderson et al. |
| 7,006,874 B2 | 2/2006 | Knowlton et al. |
| 7,013,179 B2 | 3/2006 | Carter et al. |
| 7,022,121 B2 | 4/2006 | Stern et al. |
| 7,077,840 B2 | 7/2006 | Altshuler et al. |
| 7,115,123 B2 | 10/2006 | Knowlton et al. |
| 7,115,124 B1 | 10/2006 | Xiao |
| 7,118,563 B2 | 10/2006 | Weckwerth et al. |
| 7,141,049 B2 | 11/2006 | Stern et al. |
| 7,153,298 B1 | 12/2006 | Cohen |
| 7,204,832 B2 | 4/2007 | Altshuler et al. |
| 7,234,239 B2 | 6/2007 | Saito et al. |
| 7,238,183 B2 | 7/2007 | Kreindel |
| 7,251,531 B2 | 7/2007 | Mosher et al. |
| 7,266,414 B2 | 9/2007 | Cornelius et al. |
| 7,275,819 B2 | 10/2007 | Bleau |
| 7,278,991 B2 | 10/2007 | Morris et al. |
| 7,278,993 B2 | 10/2007 | Kelly et al. |
| 7,416,550 B2 | 8/2008 | Protsenko et al. |
| 7,435,247 B2 | 10/2008 | Woloszko et al. |
| 7,494,488 B2 | 2/2009 | Weber |
| 7,517,344 B2 | 4/2009 | Van Hal et al. |
| 7,601,149 B2 | 10/2009 | DiCarlo et al. |
| 7,643,874 B2 | 1/2010 | Nitzan et al. |
| 7,713,266 B2 | 5/2010 | Elkins et al. |
| 7,771,419 B2 | 8/2010 | Carmel et al. |
| 7,824,394 B2 | 11/2010 | Manstein |
| 7,935,107 B2 | 5/2011 | Altshuler et al. |
| 7,963,985 B2 | 6/2011 | Minamoto et al. |
| 8,021,360 B2 | 9/2011 | Dunning et al. |
| 8,034,052 B2 | 10/2011 | Podhajsky |
| 8,109,927 B2 | 2/2012 | Kelly et al. |
| 8,128,622 B2 | 3/2012 | Podhajsky et al. |
| 8,133,191 B2 | 3/2012 | Rosenberg et al. |
| 8,133,216 B2 | 3/2012 | Knopp et al. |
| 8,135,475 B2 | 3/2012 | Kreindel et al. |
| 8,157,807 B2 | 4/2012 | Ferren et al. |
| 8,202,268 B1 | 6/2012 | Wells et al. |
| 8,206,381 B2 | 6/2012 | Lischinsky et al. |
| 8,235,989 B2 | 8/2012 | Palanker et al. |
| 8,273,037 B2 | 9/2012 | Kreindel et al. |
| 8,292,882 B2 | 10/2012 | Danek et al. |
| 8,506,564 B2 | 8/2013 | Long et al. |
| 2001/0007068 A1 | 7/2001 | Ota et al. |
| 2001/0014819 A1 | 8/2001 | Ingle et al. |
| 2002/0010414 A1 | 1/2002 | Coston et al. |
| 2002/0035363 A1 | 3/2002 | Edwards et al. |
| 2002/0058936 A1 | 5/2002 | Avrahami et al. |
| 2002/0082543 A1 | 6/2002 | Park et al. |
| 2002/0104543 A1 | 8/2002 | Hollander et al. |
| 2002/0120256 A1* | 8/2002 | Furuno et al. ............... 606/9 |
| 2002/0120260 A1 | 8/2002 | Morris et al. |
| 2002/0120261 A1 | 8/2002 | Morris et al. |
| 2002/0128641 A1 | 9/2002 | Underwood et al. |
| 2002/0128648 A1 | 9/2002 | Weber et al. |
| 2002/0143373 A1 | 10/2002 | Courtnage et al. |
| 2002/0161324 A1 | 10/2002 | Henley et al. |
| 2002/0173780 A1 | 11/2002 | Altshuler et al. |
| 2002/0183245 A1 | 12/2002 | Hasan et al. |
| 2002/0190337 A1 | 12/2002 | House et al. |
| 2002/0193729 A1 | 12/2002 | Cormier et al. |
| 2002/0198575 A1 | 12/2002 | Sullivan |
| 2003/0004499 A1 | 1/2003 | McDaniel |
| 2003/0018255 A1 | 1/2003 | Martin et al. |
| 2003/0032900 A1 | 2/2003 | Ella |
| 2003/0032950 A1* | 2/2003 | Altshuler et al. ............ 606/9 |
| 2003/0055413 A1 | 3/2003 | Altshuler et al. |
| 2003/0055414 A1 | 3/2003 | Altshuler et al. |
| 2003/0097162 A1 | 5/2003 | Kreindel |
| 2003/0109871 A1 | 6/2003 | Johnson et al. |
| 2003/0135250 A1 | 7/2003 | Lauman et al. |
| 2003/0139790 A1 | 7/2003 | Ingle et al. |
| 2003/0185255 A1 | 10/2003 | Ye et al. |
| 2003/0195494 A1 | 10/2003 | Altshuler et al. |
| 2003/0199863 A1 | 10/2003 | Swanson et al. |
| 2003/0199946 A1 | 10/2003 | Gutwein |
| 2004/0010250 A1 | 1/2004 | Manna et al. |
| 2004/0010298 A1 | 1/2004 | Altshuler et al. |
| 2004/0015161 A1 | 1/2004 | Lovewell |
| 2004/0015162 A1 | 1/2004 | McGaffigan |
| 2004/0064167 A1 | 4/2004 | Berry et al. |

(56) References Cited

U.S. PATENT DOCUMENTS

| | | |
|---|---|---|
| 2004/0133251 A1 | 7/2004 | Altshuler et al. |
| 2004/0138603 A1 | 7/2004 | Cleary et al. |
| 2004/0143308 A1 | 7/2004 | Lundahl et al. |
| 2004/0147984 A1 | 7/2004 | Altshuler et al. |
| 2004/0167501 A1 | 8/2004 | Island et al. |
| 2004/0181216 A1 | 9/2004 | Kelly et al. |
| 2004/0186466 A1 | 9/2004 | Chornenky |
| 2004/0193234 A1 | 9/2004 | Butler |
| 2004/0210214 A1 | 10/2004 | Knowlton |
| 2004/0236320 A1 | 11/2004 | Protsenko et al. |
| 2004/0260210 A1 | 12/2004 | Ella et al. |
| 2004/0267252 A1 | 12/2004 | Washington et al. |
| 2005/0015042 A1 | 1/2005 | Sun et al. |
| 2005/0033286 A1 | 2/2005 | Eggers et al. |
| 2005/0043653 A1 | 2/2005 | Trimmer et al. |
| 2005/0049543 A1 | 3/2005 | Anderson et al. |
| 2005/0085804 A1 | 4/2005 | McGaffigan |
| 2005/0096646 A1 | 5/2005 | Wellman et al. |
| 2005/0137654 A1 | 6/2005 | Hoenig et al. |
| 2005/0137655 A1 | 6/2005 | MacFarland et al. |
| 2005/0143793 A1 | 6/2005 | Korman et al. |
| 2005/0147137 A1 | 7/2005 | Slatkine |
| 2005/0149012 A1 | 7/2005 | Penny et al. |
| 2005/0177139 A1 | 8/2005 | Yamazaki et al. |
| 2005/0288680 A1 | 12/2005 | Ingle et al. |
| 2006/0036300 A1 | 2/2006 | Kreindel |
| 2006/0058712 A1 | 3/2006 | Altshuler et al. |
| 2006/0095096 A1 | 5/2006 | DeBenedictis et al. |
| 2006/0130675 A1 | 6/2006 | Crawford |
| 2006/0149343 A1 | 7/2006 | Altshuler et al. |
| 2006/0200213 A1 | 9/2006 | McDaniel |
| 2006/0206173 A1 | 9/2006 | Gertner et al. |
| 2006/0224217 A1 | 10/2006 | Burgmann et al. |
| 2006/0231568 A1 | 10/2006 | Lynn et al. |
| 2006/0247741 A1 | 11/2006 | Hsu et al. |
| 2006/0253112 A1 | 11/2006 | Suarez et al. |
| 2006/0259102 A1 | 11/2006 | Slatkine |
| 2006/0271028 A1 | 11/2006 | Altshuler et al. |
| 2007/0009542 A1 | 1/2007 | Levin et al. |
| 2007/0016117 A1 | 1/2007 | Sliwa et al. |
| 2007/0038206 A1 | 2/2007 | Altshuler et al. |
| 2007/0093798 A1 | 4/2007 | DeBenedictis et al. |
| 2007/0106349 A1 | 5/2007 | Karni et al. |
| 2007/0129711 A1 | 6/2007 | Altshuler et al. |
| 2007/0129771 A1 | 6/2007 | Kurtz et al. |
| 2007/0142881 A1 | 6/2007 | Hennings |
| 2007/0191821 A1 | 8/2007 | Boxer Wachler |
| 2007/0191827 A1 | 8/2007 | Lischinsky et al. |
| 2007/0197895 A1 | 8/2007 | Nycz et al. |
| 2007/0198004 A1 | 8/2007 | Altshuler et al. |
| 2007/0213696 A1 | 9/2007 | Altshuler et al. |
| 2007/0239142 A1 | 10/2007 | Altshuler et al. |
| 2007/0239143 A1* | 10/2007 | Altshuler et al. ............ 606/9 |
| 2007/0239152 A1 | 10/2007 | Trezon |
| 2007/0271714 A1* | 11/2007 | Adam et al. ............ 15/22.2 |
| 2008/0004678 A1 | 1/2008 | Kreindel |
| 2008/0071334 A1 | 3/2008 | Hoenig et al. |
| 2008/0082090 A1 | 4/2008 | Manstein |
| 2008/0123238 A1 | 5/2008 | Campos et al. |
| 2008/0139901 A1 | 6/2008 | Altshuler et al. |
| 2008/0139974 A1 | 6/2008 | Da Silva |
| 2008/0154247 A1 | 6/2008 | Dallarosa et al. |
| 2008/0183167 A1 | 7/2008 | Britva et al. |
| 2008/0188846 A1 | 8/2008 | Palanker et al. |
| 2008/0200910 A1 | 8/2008 | Burger et al. |
| 2008/0214986 A1 | 9/2008 | Ivorra et al. |
| 2008/0214988 A1 | 9/2008 | Altshuler et al. |
| 2008/0215124 A1 | 9/2008 | Wagenaar et al. |
| 2008/0221504 A1 | 9/2008 | Aghion |
| 2008/0274166 A1 | 11/2008 | Sacks et al. |
| 2008/0294153 A1 | 11/2008 | Altshuler et al. |
| 2008/0306476 A1 | 12/2008 | Hennings et al. |
| 2009/0034263 A1 | 2/2009 | Stenback et al. |
| 2009/0036953 A1 | 2/2009 | Gustavsson |
| 2009/0043293 A1 | 2/2009 | Pankratov et al. |
| 2009/0105706 A1 | 4/2009 | Livneh |
| 2009/0112205 A1 | 4/2009 | McGill et al. |
| 2009/0171341 A1 | 7/2009 | Pope et al. |
| 2009/0182315 A1 | 7/2009 | Zigan et al. |
| 2009/0192503 A1 | 7/2009 | Epshtein et al. |
| 2009/0222023 A1 | 9/2009 | Boone et al. |
| 2009/0234341 A1 | 9/2009 | Roth |
| 2009/0234342 A1 | 9/2009 | Ely et al. |
| 2009/0240310 A1 | 9/2009 | Kennedy |
| 2009/0299361 A1 | 12/2009 | Flyash et al. |
| 2010/0010480 A1 | 1/2010 | Mehta et al. |
| 2010/0063565 A1 | 3/2010 | Beerwerth et al. |
| 2010/0145321 A1 | 6/2010 | Altshuler et al. |
| 2010/0185193 A1 | 7/2010 | Kreindel |
| 2010/0185194 A1 | 7/2010 | Kreindel |
| 2010/0198134 A1 | 8/2010 | Eckhouse et al. |
| 2010/0211055 A1 | 8/2010 | Eckhouse et al. |
| 2010/0249772 A1 | 9/2010 | Mehta et al. |
| 2010/0274329 A1 | 10/2010 | Bradley et al. |
| 2011/0015549 A1 | 1/2011 | Eckhouse et al. |
| 2011/0137386 A1 | 6/2011 | Kreindel |
| 2011/0166559 A1 | 7/2011 | Eckhouse et al. |
| 2011/0196363 A1 | 8/2011 | Kreindel |
| 2012/0016354 A9 | 1/2012 | Epshtein et al. |
| 2012/0022435 A1 | 1/2012 | Ignon et al. |
| 2012/0022504 A1 | 1/2012 | Epshtein et al. |
| 2012/0022512 A1 | 1/2012 | Vaynberg |
| 2012/0022518 A1 | 1/2012 | Levinson |
| 2012/0123397 A1 | 5/2012 | Epshtein et al. |
| 2012/0143178 A9 | 6/2012 | Mehta |
| 2012/0143270 A1 | 6/2012 | Mehta |
| 2012/0197242 A1 | 8/2012 | Rosenberg |
| 2012/0290023 A1 | 11/2012 | Boyden et al. |
| 2013/0144280 A1 | 6/2013 | Eckhouse et al. |
| 2013/0289679 A1 | 10/2013 | Eckhouse et al. |

FOREIGN PATENT DOCUMENTS

| | | |
|---|---|---|
| JP | 06113920 A2 | 4/1994 |
| JP | 11132843 A2 | 12/1999 |
| JP | 2003034630 | 2/2003 |
| WO | WO-83/02389 A1 | 7/1983 |
| WO | WO-93/21992 A1 | 11/1993 |
| WO | WO-99/09143 A1 | 2/1999 |
| WO | WO-9909143 A1 | 2/1999 |
| WO | WO-99/34867 A1 | 7/1999 |
| WO | WO-02/078644 A2 | 10/2002 |
| WO | WO-02078644 A2 | 10/2002 |
| WO | WO-03/039367 A1 | 5/2003 |
| WO | WO-03039367 A1 | 5/2003 |
| WO | WO-2006/128034 A1 | 11/2006 |
| WO | WO 2007137304 A2 | 11/2007 |

OTHER PUBLICATIONS

PCT/IL09/00033 International Search Report.
PCT/IL09/00695 International Search Report.
PCT/IL09/00817 International Search Report.
PCT/IL2010/001025 International Search Report.
PCT/IL10/00222 International Search Report.
PCT/IL10/00751 International Search Report.
PCT/IL11/00170 International Search Report.
PCT/IL11/00256 International Search Report.
PCT/IL11/00630 International Search Report.

* cited by examiner

DETAIL I-I.

HAIR REMOVAL APPARATUS FOR PERSONAL USE AND THE METHOD OF USING SAME

CROSS-REFERENCE TO RELATED APPLICATIONS

This is a non-provisional application filed in the United States Patent Office under 37 CFR 1.53(b) and 35 U.S.C. 111 as a divisional of the presently pending United States Patent Application for patent Ser. No. 12/355,749 filed on Jan. 16, 2009, which application claims priority to United States Provisional Application for patent that was filed on Jan. 17, 2008 and assigned Ser. No. 61/021,723, and of the United States Provisional Application for patent that was filed on Apr. 16, 2008 and assigned Ser. No. 61/045,282, all of which are hereby incorporated by reference.

BACKGROUND

The method and apparatus disclosed herein are related to the field of personal cosmetic procedures and in particular to hair removal procedures.

External appearance is important to practically everybody. In recent years, methods and apparatus have been developed for different cosmetic treatments. Among these cosmetic treatments includes hair removal, treatment of vascular lesions, skin rejuvenation, as well as others. In some of these treatments, the skin surface is illuminated by visible or infra red (IR) radiation, generally termed optical radiation, to heat lower tissue volumes to a sufficiently high temperature so as to achieve a desired effect, which is typically in the range of 38-80 degrees Celsius. One such desired effect may include weakening of the hair follicle or root destruction. Another desired effect may include hair re-growth retardation, which is typically achieved by illumination of earlier depilated skin surface by laser, LED, Xenon lamp, Intense Pulsed Light (IPL), or incandescent lamp radiation, generally termed optical radiation. The optical radiation may have a single wavelength, such as is the case with lasers, or several wavelengths as is the case for incandescent lamps. The wavelengths are selected to be optimal for the color of the contrasted component of the treated skin segment and are typically in the range of 400 to 1800 nm.

Presently, a number of Radio Frequency (RF) based methods for treatment of deeper skin or tissue layers have been developed and are available. In these methods, electrodes are applied to the skin and an RF voltage in pulse or continuous waveform (CW) is applied across the electrodes. The properties of the RF voltage are selected to generate RF induced current in a volume of tissue to be treated. The current heats the tissue to the required temperature, which is typically in the range of 38-80 degrees Celsius.

However, the above-described equipment that utilizes electrodes is both costly and bulky. Further, such equipment is typically operated in an ambulatory set-up by a qualified operator and frequently requires the presence of medical personnel specialized in such treatments. Therefore, there is a need in the art for a small size, low cost, and safe to use apparatus that may be operated by the user, enabling him/her to conduct skin treatment and get results similar or identical to those provided by professional equipment used for skin treatments.

GLOSSARY

Several terms are utilized throughout this disclosure. The definitions for these terms are provided here for convenience.

The term "illumination sources" and "light sources" as used in the present disclosure has the same meaning and includes sources of visible and invisible infrared radiation.

As used herein, the term "hair removal" includes partial or complete hair removal from the treated skin surface as well as hair re-growth retardation.

The term "skin surface" relates to the most external skin layer, which may be stratum corneum.

The term "tissue" relates to skin layers located below the stratum corneum. The layers may be located immediately below the stratum corneum and as deep as 6 or even 7 mm below the stratum corneum.

BRIEF SUMMARY

Various embodiments are directed towards an apparatus, system or method of providing complete or partial hair removal and hair growth deterrent. The embodiments may include various elements that may include, but are not limited or required in all embodiments. Some of these elements are: (a) a mechanical process for cutting, plucking or shaving hair follicles; (b) integrated and/or removable cartridges to provide the application of heat and/or energy to the skin surface before, after and/or during the application of the mechanical process; (c) further skin treatment techniques including the application of solutions before, after and/or during the mechanical process and/or the application of heat and/or energy. Overall, the various embodiments operate to treat an area of skin to facilitate the removal of all or a portion of hair, retard further growth, and recovery or health maintenance of the skin surface.

BRIEF DESCRIPTION OF THE SEVERAL VIEWS OF THE DRAWING

The disclosure is provided by way of non-limiting examples only, with reference to the accompanying drawings, in which like reference characters refer to the same parts throughout the different views. The drawings are not necessarily to scale, emphasis instead being placed upon illustrating the principles of the method.

DETAILED DESCRIPTION OF EXEMPLARY EMBODIMENTS

The principles and execution of the apparatus and the method described thereby may be understood with reference to the drawings and the accompanying description of non-limiting, exemplary embodiments.

Figure 1:
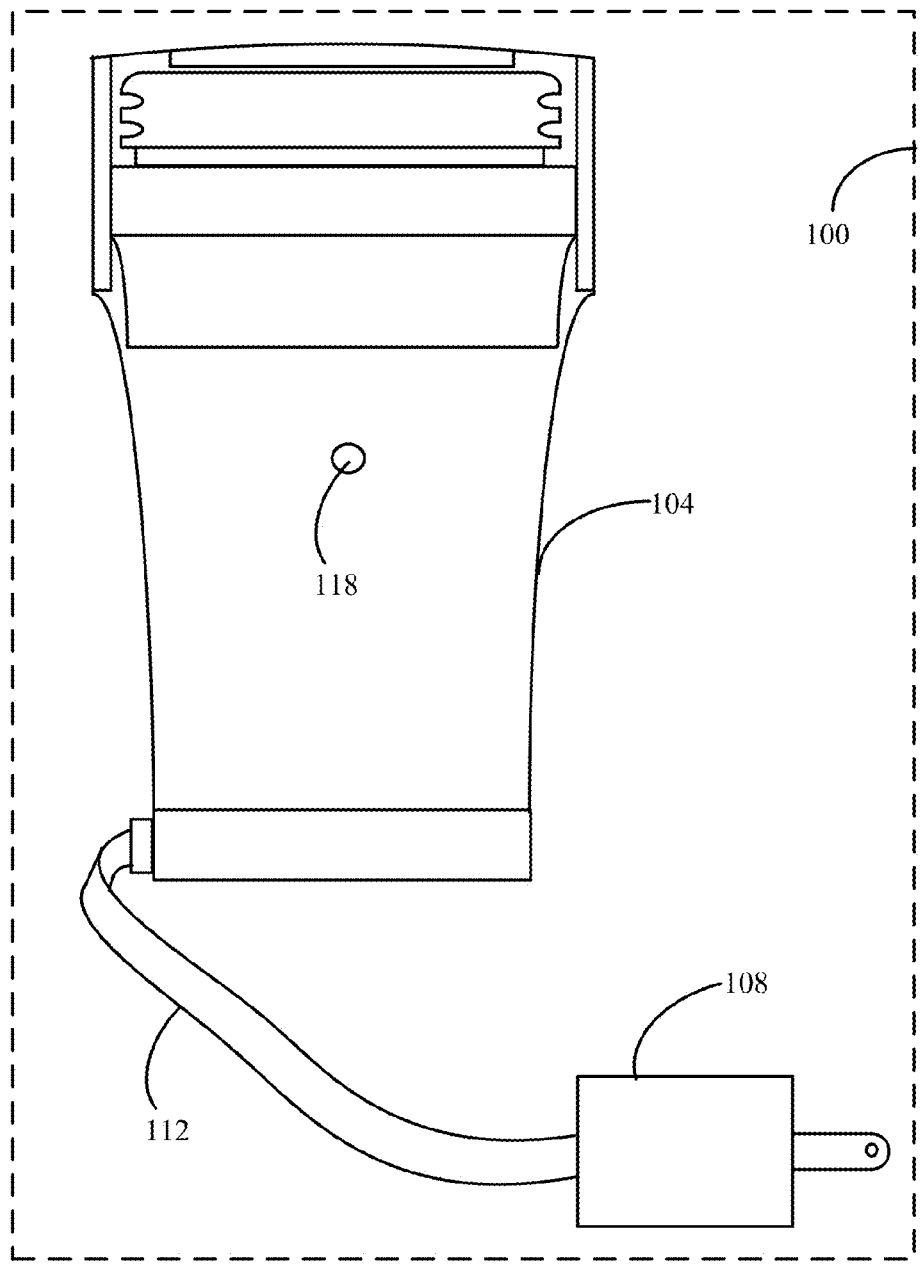
FIG. 1 is a schematic illustration of an exemplary embodiment of the apparatus for personal use for hair removal.

Reference is made to FIG. 1, which is a schematic illustration of an exemplary embodiment of the apparatus for personal hair removal. Apparatus 100 comprises an applicator 104 adapted for sliding movement on a subject skin, a charging device 108, and a harness 112 connecting between applicator 104 and charging device 108. Harness 112 enables electric communication between applicator 104 and charging device 108. Apparatus 100 may receive power supply from a regular electric supply network receptacle, or from a rechargeable or regular battery. LED 118 indicates operational status of applicator 104.

Figure 2A:
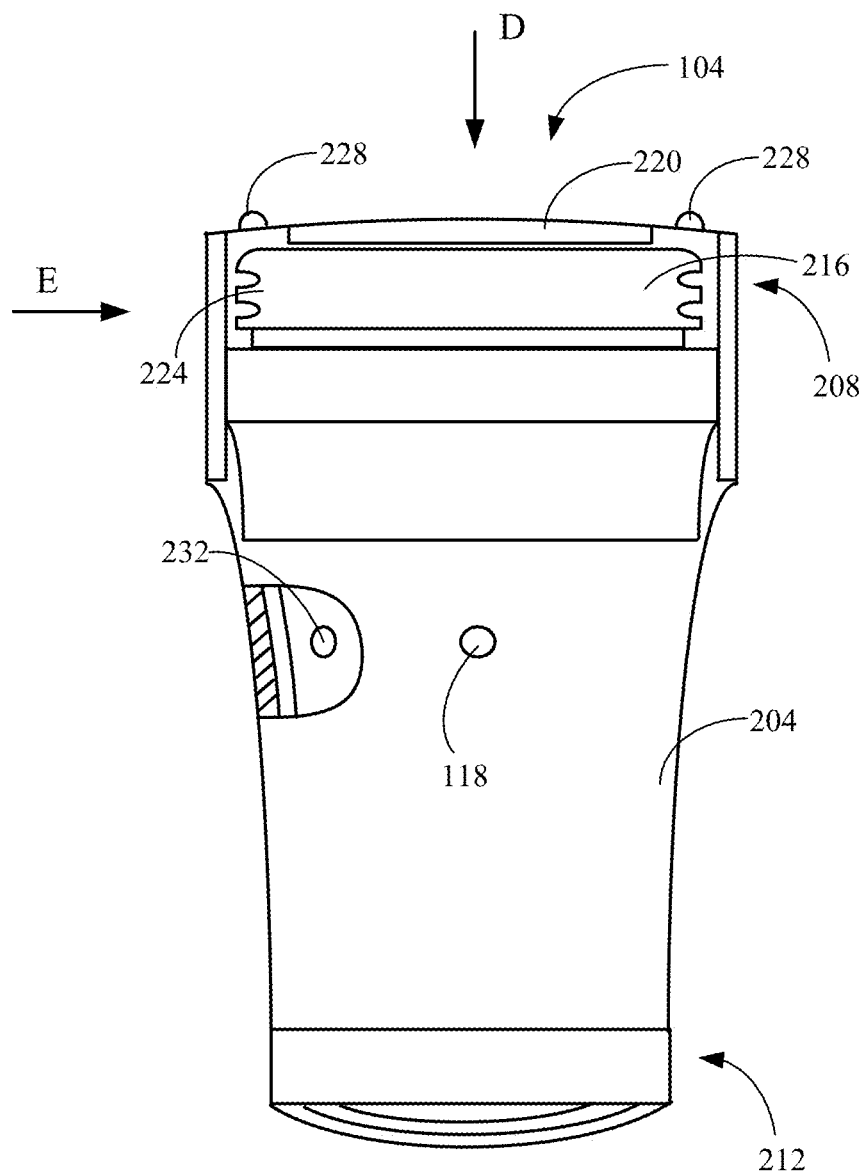
FIGS. 2A-2C are schematic illustrations of the first exemplary embodiment of the applicator of the apparatus of FIG. 1.
Figure 2B:
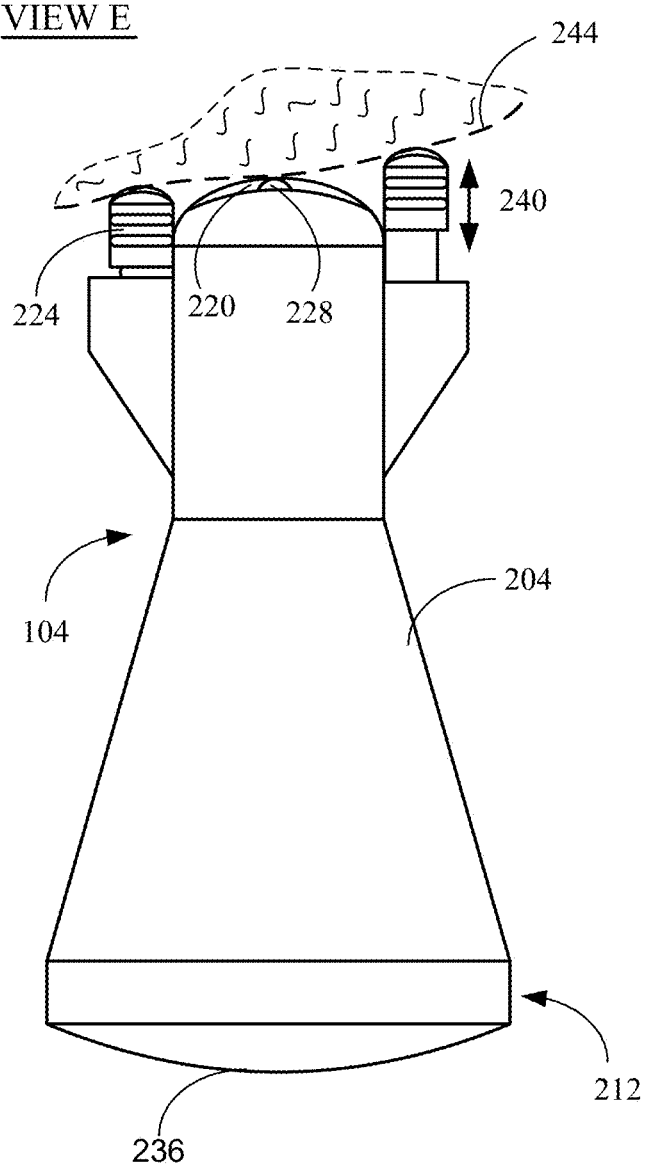
Figure 2C:
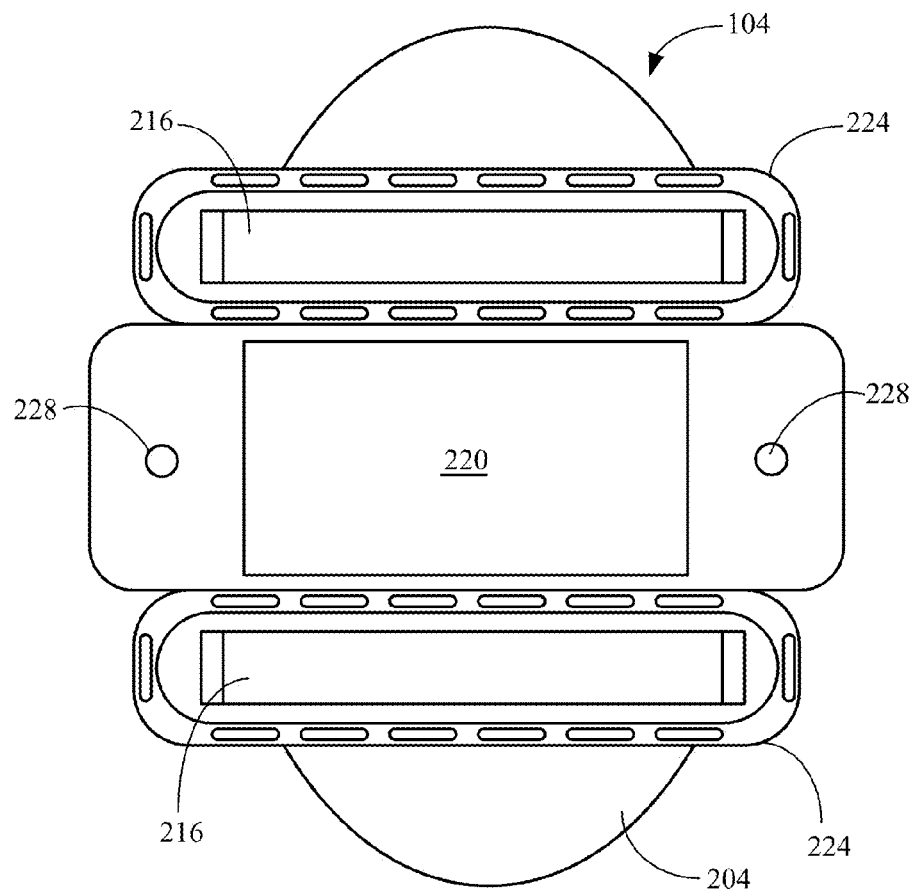

FIG. 2A is a first side planer view of a first exemplary embodiment of the applicator of the apparatus of FIG. 1. FIG. 2B is a second side planer view in the direction of arrow E of FIG. 2A of the first exemplary embodiment of the applicator of the apparatus of FIG. 1. FIG. 2C is a top planer view in the direction of arrow D of FIG. 2A of the first exemplary embodiment of the applicator of the apparatus of FIG. 1. The series of drawings represented in FIGS. 2A-2C may be referred to collectively as FIG. 2. Applicator 104 (FIG. 2A) is shown to include an ergonomically designed casing 204 which fits the hand, having a first end 208 and a second end 212. One or more illumination sources 216, at least one hair removal mechanism 220, and at least one contact to skin sensing mechanism shown as micro switches 228 for activating illumination sources 216 and a hair removal mechanism 220. Micro switches 228 are located at the first end 208 and are activated by slight pressure developed by application of applicator 104 to skin (not shown). When depressed, micro switches 228 enable one or more illumination sources 216 and other electric and electronic circuits of applicator 104. In one embodiment, illumination sources 216 and other electric and electronic circuits may each be operated independently and have their own ON and OFF switch mechanisms, for example, RF current sensing mechanism. It will also be appreciated that in some embodiments, other sensor mechanisms may also be utilized such as capacitive coupling, ground detection, a mechanical on/off switch operated by a user as well as other techniques.

The illumination sources 216 may include a variety of sources, a few non-limiting examples include an incandescent lamp, xenon lamp, laser diodes, LED, laser or even a combination of two or more of these sources as well as other sources. Illumination sources 216 may operate in a pulsed, continuous, graduated, modulated, oscillating or other operation mode as well as a combination of two or more of these modes. The power and operational times of the sources are selected to avoid potential damage to the treated segment of skin. In some embodiments each of the illumination sources 216 may be packed in a cartridge-like packaging 224 detachable from the ergonomically designed, fitting-the-hand casing 204 of applicator 104. The cartridge like packaging of the illumination source advantageously allows different illumination sources to be used with the same applicator. Each of the cartridges, like illumination sources 216 packaging 224, may be mounted on springs or a flexible mounting enabling freedom of movement of the cartridge-like packaging 224 with light source 216 in respect to applicator casing 204 as shown by arrow 240 in FIG. 2B. This allows cartridge 224 with illumination sources 216 to follow skin/casing contour 244 when applicator 104 is translated (moved) over a segment of skin to be treated. Motion direction sensor 232 senses the applicator movement direction and provides a signal for proper switching of the light sources 216.

A cooling arrangement, possibly a fan (not shown) which may be placed at a section 236 located at the second end 212 of applicator 104. The fan removes the heat generated by the operation of electric and electronic circuits and lamps or LEDs of applicator 104 and enables normal operating conditions of the applicator.

FIG. 2C is a schematic illustration of a top view of the first end 208 of the exemplary embodiment of applicator 104. FIG. 2C shows the cartridge-like packaging 224 of light source 216, hair removal mechanism 220, and micro switches 228.

Figure 3A:
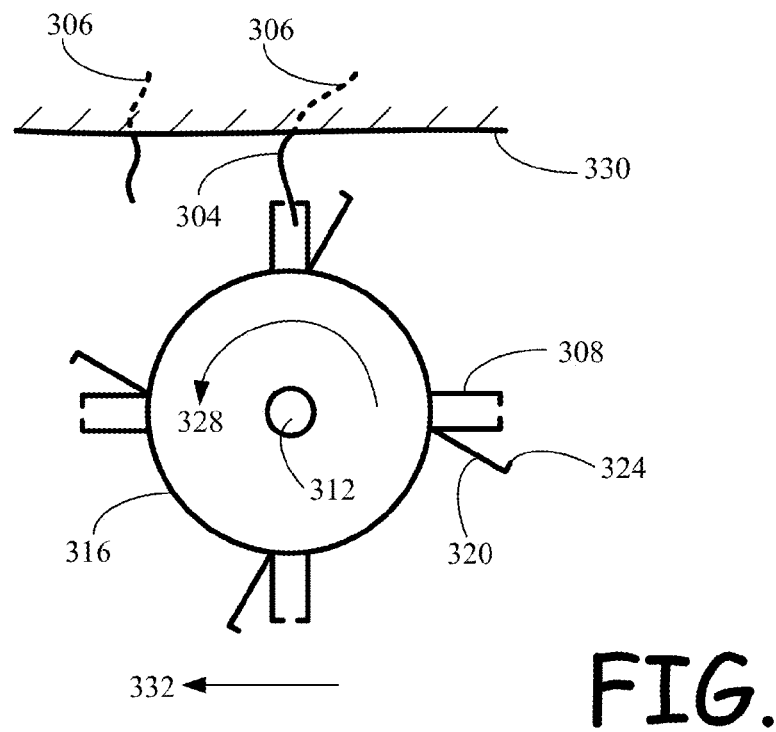
FIGS. 3A-3D are schematic illustrations of an exemplary embodiment of a hair removal mechanism of the applicator.
Figure 3B:
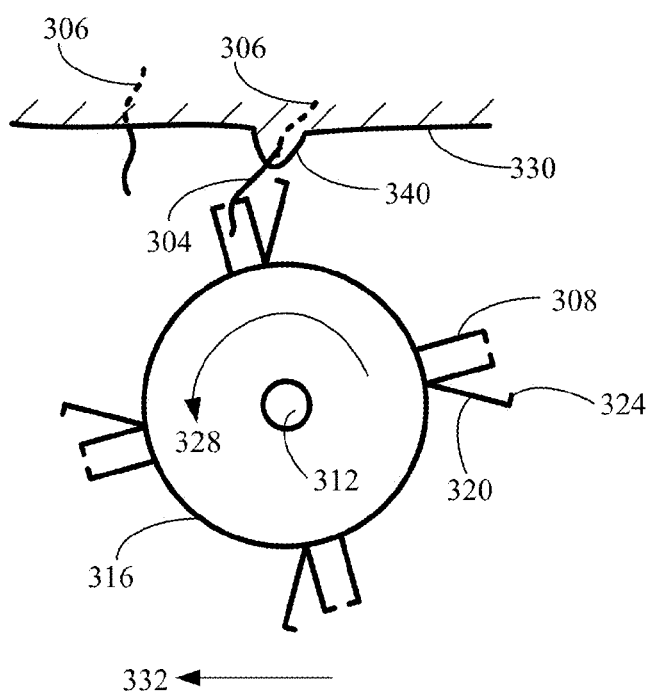

FIG. 3A illustrates a first state of the operation of an exemplary hair removal mechanism in operation. FIG. 3B illustrates a second state of operation of the exemplary hair removal mechanism in operation. In the exemplary embodiment illustrated in FIG. 3A, hair removal mechanism 220 may include at least one, and in some embodiments more than one, set of tweezers 308 attached to a holder 316 rotating around axis 312. Adjacent to tweezers 308 attached to the same axes is a lever 320 terminated by a blade 324. Alternatively, lever 320 may be rigidly coupled to tweezers 308 to ensure a constant follow-up after tweezers 308. There is a preset difference or offset between the location of tweezers 308 and the location of blades 324 of lever 320 with respect to skin 330. Typically, blade 324 would be located closer to skin 330 than tweezers 308. The difference in the location of blade 324 and tweezers 308 may be regulated according to the type of skin, hair, and particular treated segment of the subject casing.

For hair 304 removal, tweezers 308 are applied to skin 330. Holder 316 rotates in the direction indicated by arrow 328 and concurrently with rotation may move linearly on the surface of skin 330 in the direction indicated by arrow 332. As tweezers 308 continue to rotate to the second state, they pick-up at least one hair shaft or follicle 304 (FIG. 3B) and begin pulling it out of skin 330. A pulling force generated by the rotation of tweezers 308 and assisted by linear movement of holder 316 applied to hair shaft 304 pulls together with hair shaft 304, skin 330 surrounding the hair shaft and follicle. This force deforms skin 330 and forms a type of goose bump or goose pimple 340 protruding over the rest of the skin surface surrounding the follicle. Blade 324 cuts hair 304 (FIG. 3C) substantially close to the peak of goose bump 340. The pulling force is set to a particular tension with respect to the hair that is sufficient to impose a tension on the hair shaft but not enough to pull the hair shaft out of the skin.

Figure 4:
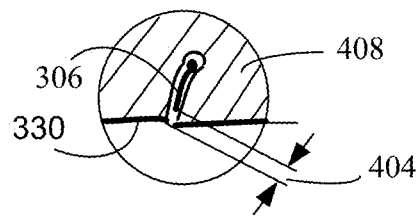
FIG. 4 is a magnified schematic illustration of a cut and retracted back hair follicle (shaft).

FIG. 4 is a magnified schematic illustration of a cut and retracted back hair shaft or follicle. Following the cut of hair shaft 304, skin 330 that formed goose bump 340, retracts or returns to its normal at rest state. The residuals 306 of hair shaft 304 retract to the original position. The residual 306 of hair shaft 304 retracts deeper than skin surface or stratum corneum 330, such distance being indicated by numeral 404 (FIG. 4), which marks the difference in the locations of the cut end of the residual 306 of the hair shaft 304 and skin surface 330. As can be seen in the figure, the end of the residual 306 resides substantially below skin surface 330. Numeral 408 indicates the underlying tissue.

Figure 3C:
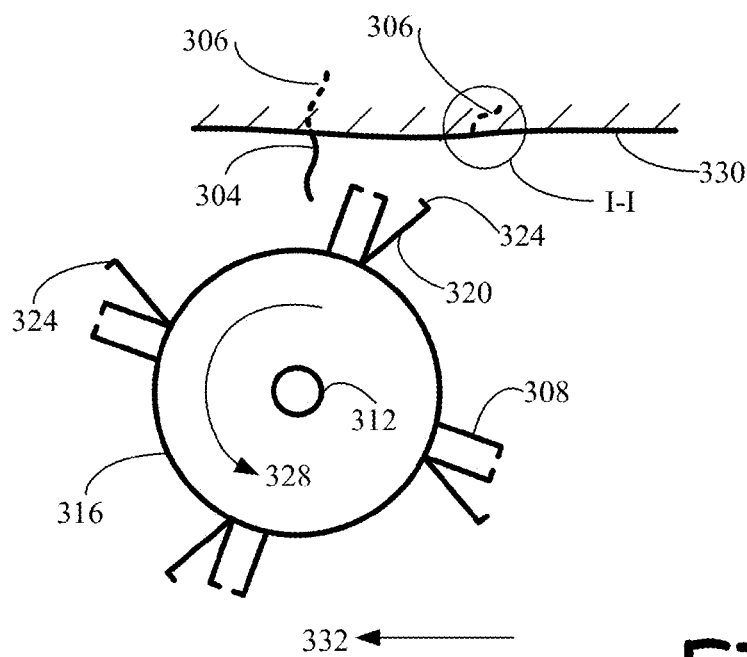
Figure 3D:
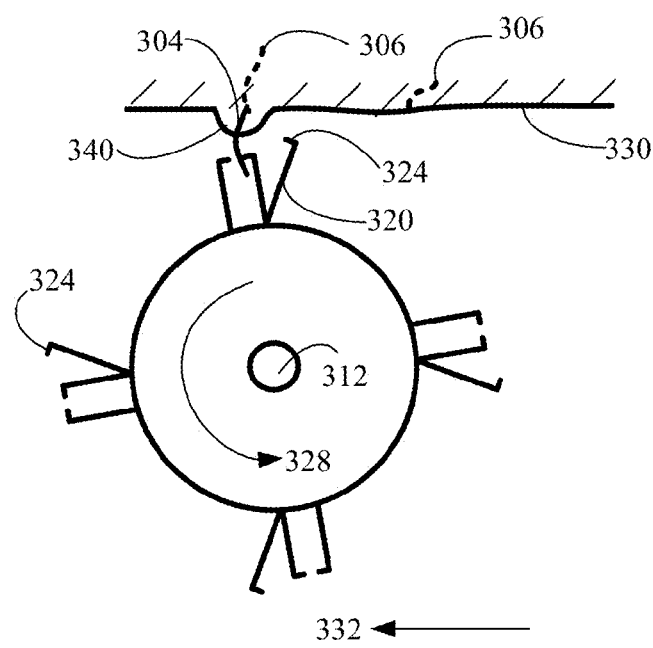

FIG. 3C illustrates a third state of the operation of the exemplary hair removal mechanism in operation. FIG. 3D illustrates a fourth state of operation of the exemplary hair removal mechanism in operation. Holder 316 (FIGS. 3C and 3D) continues to rotate in the direction indicated by arrow 328 and move linearly or in any other type of motion on the surface of skin 330 in the direction indicated by arrow 332. In the third state, tweezers 308 catch another hair shaft 304 and form bump 340 in the fourth operational state in a way similar to the one explained above. Next, hair 304 is cut in a way similar to the way that the previous hair shaft was cut. The tweezers 308 and blades 324 may be orientated in the same direction or staggered and oriented in different directions. When some of the tweezers 308 and blades 324 are oriented in different directions, the user may move back along the earlier treated skin segment and still be efficacious. When tweezers 308 and blades 324 are orientated in the same direction the user at the end of treatment stroke may rotate applicator 104 and move it in the opposite direction or simply reposition it to treat the next skin segment.

Alternatively, the hair removal mechanism 220 may be any one of the well-known mechanical hair removal mechanisms such as a razor, shaving, or an electric shaver such as for example, feminine electric shaver commercially available from Braun GmbH, Germany—model 3470 SOFTPERFECT. This model also includes other detachable heads of plucking and tweezing mechanisms. Similar or even the same mechanisms are also, of course, applicable to male hair removal/shavers. The illumination head/s may be attached and operate with a conventional epilator with only one head of either a shaver or epilator, or even a razor. The hair removal mechanism may be an exchangeable mechanism, where the mechanism most appropriate for the task is assembled on the applicator.

Illumination sources 216 (FIG. 2) may operate simultaneously with hair removal mechanism 220. However; they illuminate a different segment of skin from which hair removal mechanism 220 has already removed hair. Illumination destroys or weakens hair follicles and roots that are occasionally left, and should follow mechanical hair epilation. In order to synchronize the operation of illumination sources 216 with hair removal mechanism 220, a motion direction sensor, or even just a direction sensor (not shown) that switches between light sources 216 equips applicator 104. The direction sensor may be of different types, for example, a rotating wheel with a plurality of openings to modulate a source of light, a mechanical switch of any type, an optical mouse type direction sensor, an accelerometer, pressure sensors on the applicator 104 and others. Further, the direction sensor may determine displacement speed and trigger an off state if the displacement speed is lower than a target value or an on state if the displacement speed is above a target value. It will be appreciated that hysteresis may be applied in entering and exiting the on and off states. For instance, the threshold displacement speed to trigger the on state may be higher than the displacement speed to trigger the off state. In addition, the hysteresis effect may be obtained also by utilizing a time delay. For instance, once the on state is entered, a time delay can be set to prevent entrance into the off state during a desired delay. Likewise, once the off state is entered, another time delay can be utilized to prevent the on state from being immediately entered again. Activation of the illumination sources by direction sensors alleviates occasional skin burns or other treatment side effects, since illumination sources are operative only when the applicator moves over the skin in a minimum velocity. Moreover, it is possible to ensure that the appropriate illumination source illuminating the treated skin segment is activated based on the direction of advance of the applicator 104. Illumination sources 216 operate typically in continuous or pulse operation mode, but may also include any of the above-mentioned, or a combination of two or more of the above-mentioned operation modes, as well as other modes.

Figure 5:
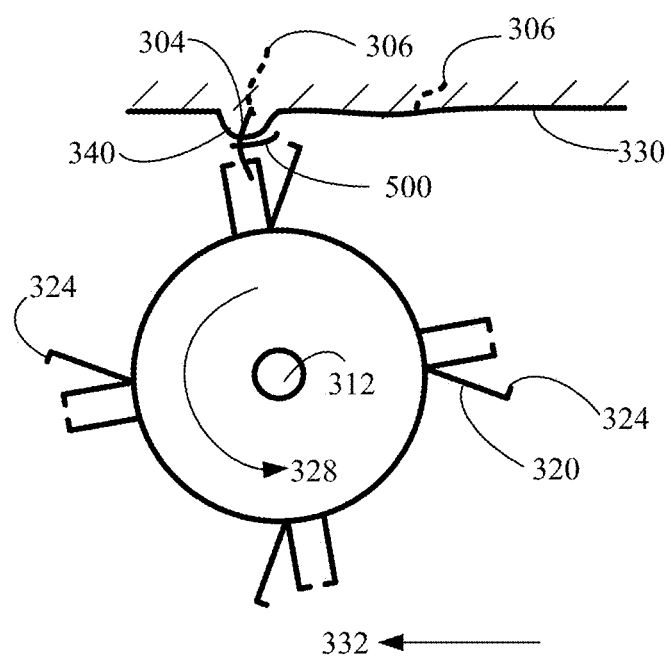
FIG. 5 is a schematic illustration of the second exemplary embodiment of the hair removal mechanism of the applicator.

FIG. 5 is a schematic illustration of the second exemplary embodiment of the hair removal mechanism. A comb type protective plate 500 protects skin 330 and especially bumps 340 from occasional damage by rotating blades 324 (FIG. 3). The comb type protecting plate 500 may be attached to the applicator 104 or held independently by a user. Blades 324 may be replaced by a fixed blade, which would cut hair 304 pulled by tweezers 308. In such embodiments, holder 316 in addition to rotation may have a linear motion. Alternatively, two comb-like blades linearly sliding with respect to each other may be implemented to cut the hair.

Figure 6A:
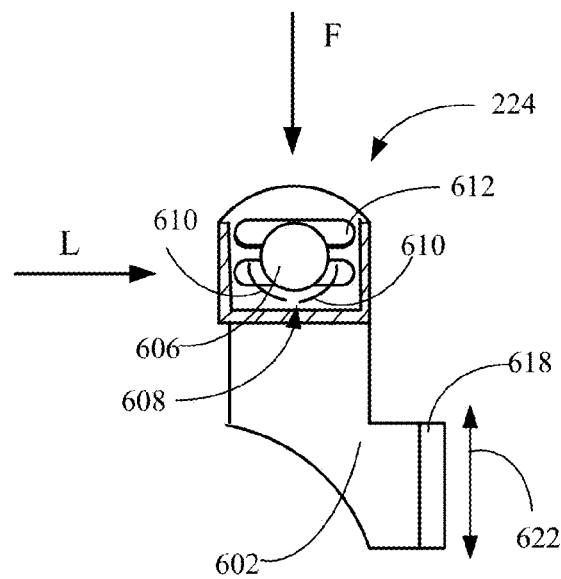
FIGS. 6A-6C are schematic illustrations of an exemplary embodiment of an illumination cartridge of the applicator.
Figure 6B:
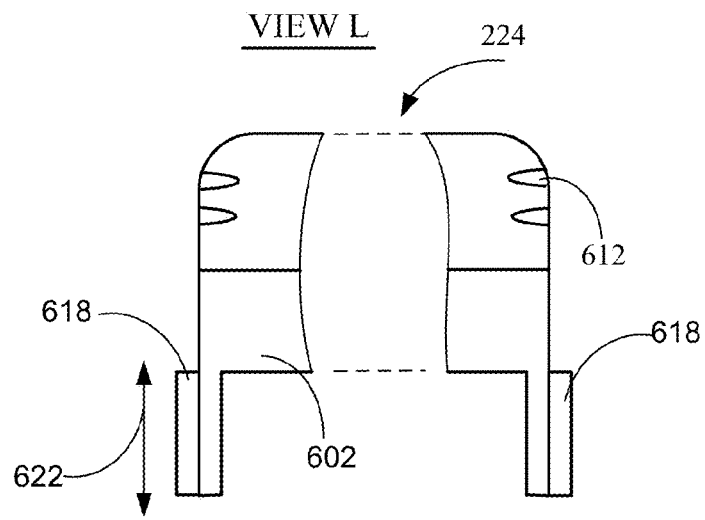
Figure 6C:
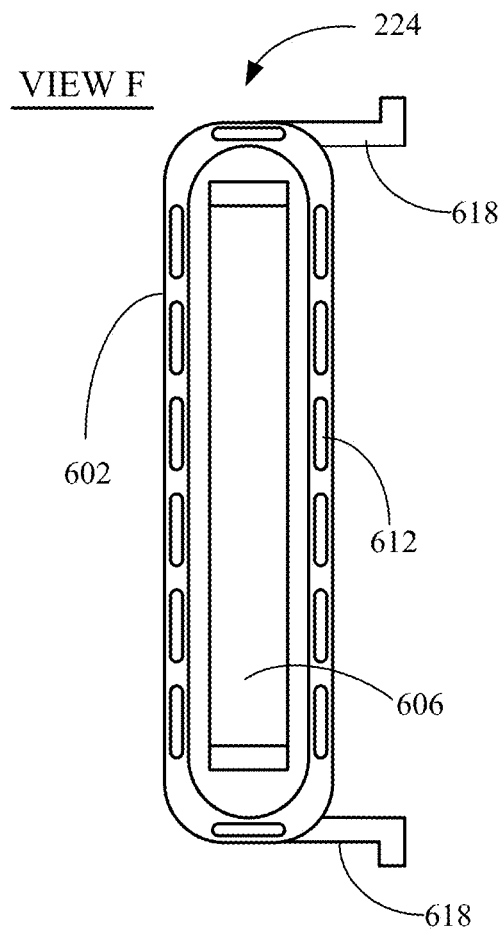

FIGS. 6A, 6B and 6C, collectively referred to as FIG. 6, depict a schematic illustration of an exemplary embodiment of an illumination cartridge of the applicator. Enclosure 602, which may be constructed of plastic, of cartridge 224 incorporates a source of illumination such as an incandescent lamp, xenon flash lamp, laser diode, LED, laser or a combination of two or more of these sources as well as others. FIG. 6A illustrates cartridge 224 with a xenon lamp 606 and a reflector 610 configured to collect a large part of the irradiance emitted by the xenon lamp 606 and direct it towards the treated segment of skin.

Plastic enclosure 602 of cartridge 224 includes two guides 618 supporting easy cartridge 224 insertion and cartridge movement along a direction indicated by arrow 622. The disclosed cartridge construction allows the treated skin segment contour 244 to be easily followed, as shown in FIG. 2B, and uniform illumination maintained of the treated skin segment. In one embodiment, cartridge 224 movement is utilized to replace micro switches 228. This may be enabled by allowing the pressed-in cartridge 224 to activate electrical and electronic circuits of applicator 104 in a mode similar to that of micro switches 228. Alternatively, guides 618 may be metalized and their descent would come in contact with a conductor and thereby close an electric circuit. It is also possible to have a section of guides to be transparent and another section opaque. Linear movement of such guide can modulate a light beam and activate or deactivate the electrical and electronic circuits of applicator 104. As will be explained below, additional methods of replacing micro switches by other sensing and switching mechanisms can be used.

Reflector 610 is shown to be constructed from two similar halves enabling free airflow for cooling lamp 606. Alternatively, a reflector formed as an integral body with respective air intake openings 608 may be used. Reflector openings 608 cooperate with respective air vents or air intake openings 612 enabling convective cooling of lamp 606 or LEDs (not shown).

Figure 7A:
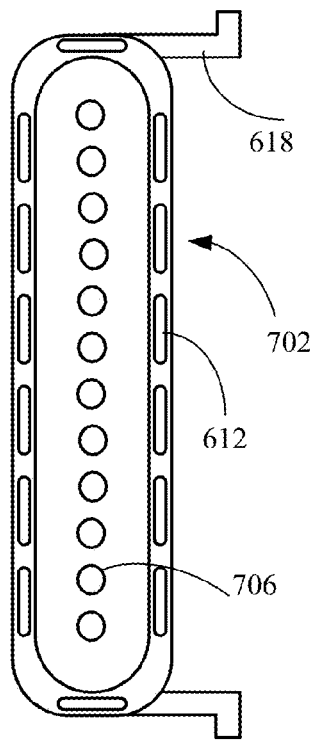
FIGS. 7A-7B are schematic illustrations of additional exemplary light source configuration of the applicator.
Figure 7B:
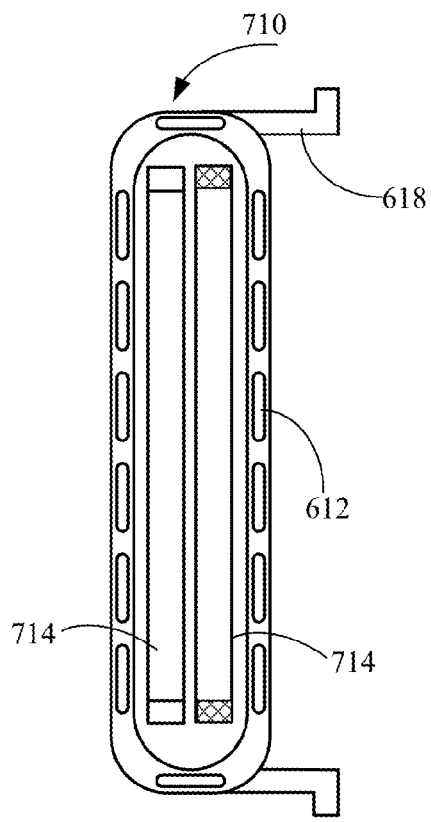

FIGS. 7A and 7B, collectively referred to as FIG. 7, depict a schematic illustration of another exemplary light source configuration of the applicator. FIG. 7A illustrates cartridge 702 similar to cartridge 224 with a plurality of LEDs 706. Each of LEDs 706 may emit a single wavelength or a plurality of wavelengths. LEDs 706 are configured to illuminate the treated segment of skin by a flux having relatively uniform flux distribution. FIG. 7B illustrates a cartridge 710 with two light sources 714, such as Xenon or other type lamps. Sources 714 may be identical sources or different light sources. Their illumination fields may overlap and they may be configured to get a desired spectrum and illumination distribution on the treated skin segment. Sources 714 may be operated simultaneously, at different or partially overlapping periods and at different operating modes e.g. pulsed, continuous or otherwise.

The described applicator architecture supports different combinations of hair removal mechanisms and illumination sources. Accordingly, a particular combination of the exchangeable hair removal mechanism and illumination sources may determine the mode of operation of the applicator. The mechanical hair removal mechanisms may be selected, for example, from a rotary-based tweezing epilator, spring type epilator, razor, or electric shaver. The illumination source may be, for example, selected from continuous or pulse operating sources as well as the other above-listed modes, sources providing a desired spectrum and illumination distribution on the treated skin segment. There may be a mix of sources operating simultaneously or at partially overlapping periods. This selection provides a wide array of combinations that may be adapted for different skin treatments.

Figure 8A:
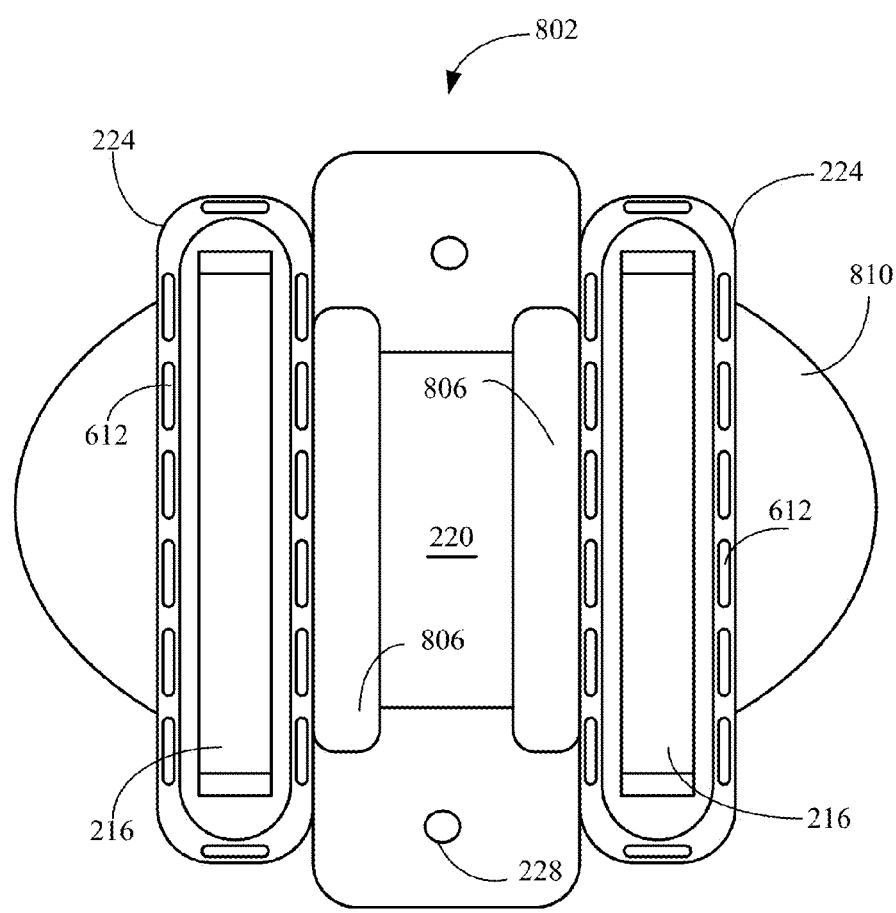
FIGS. 8A-8E are schematic illustrations of the third exemplary embodiment of the applicator.
Figure 8B:
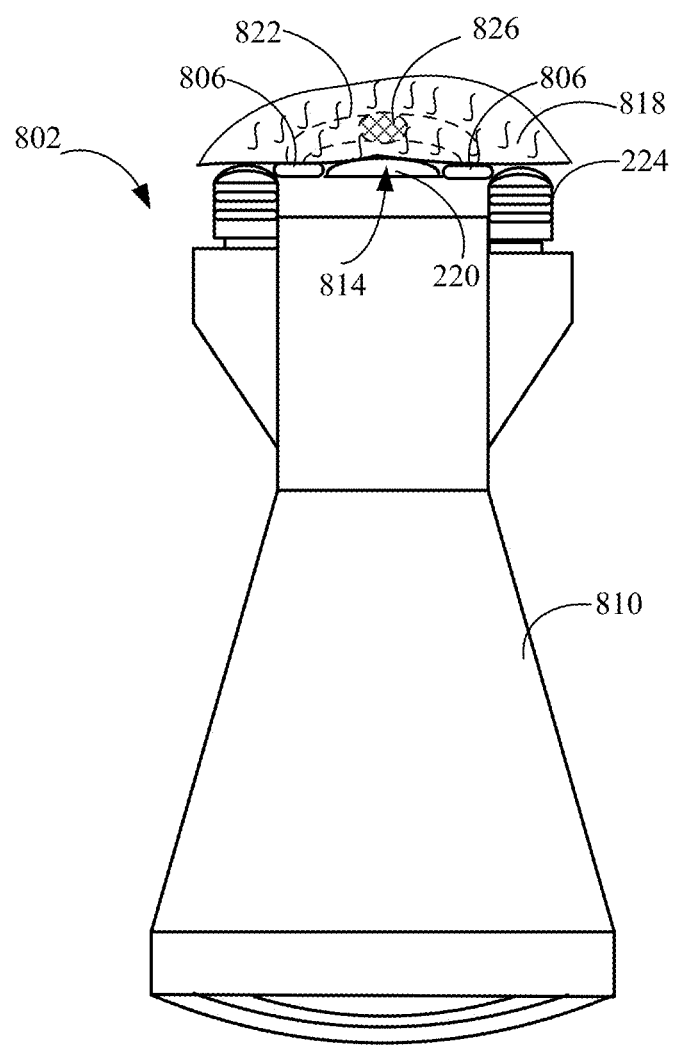
Figure 8C:
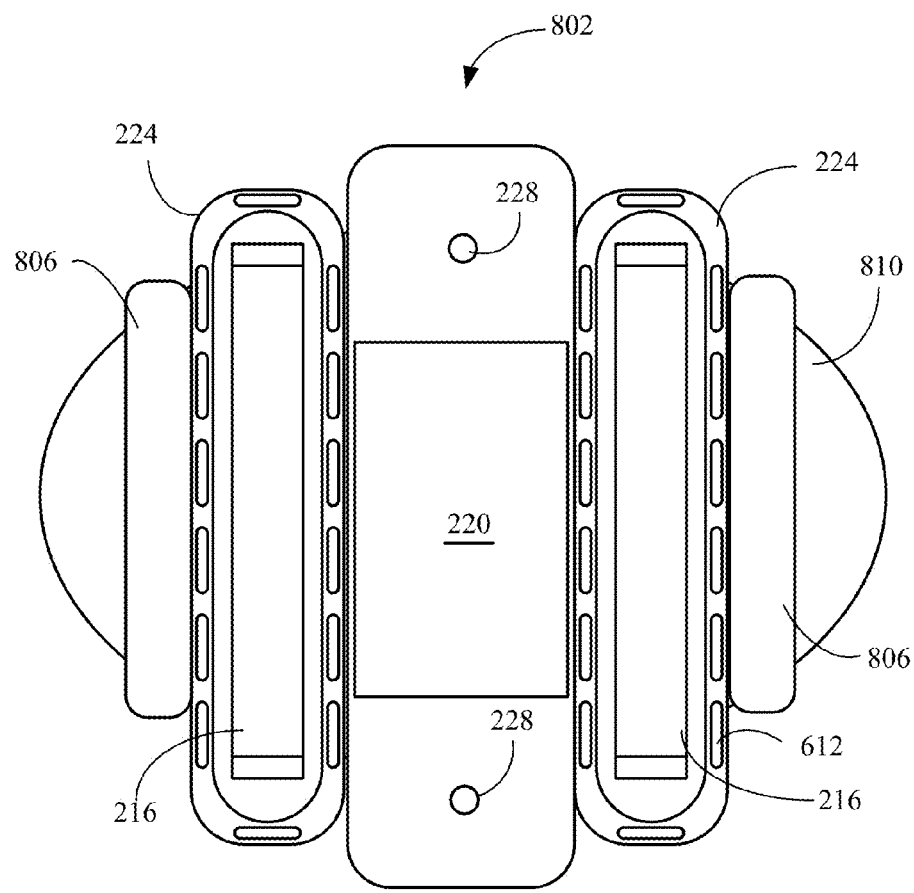
Figure 8D:
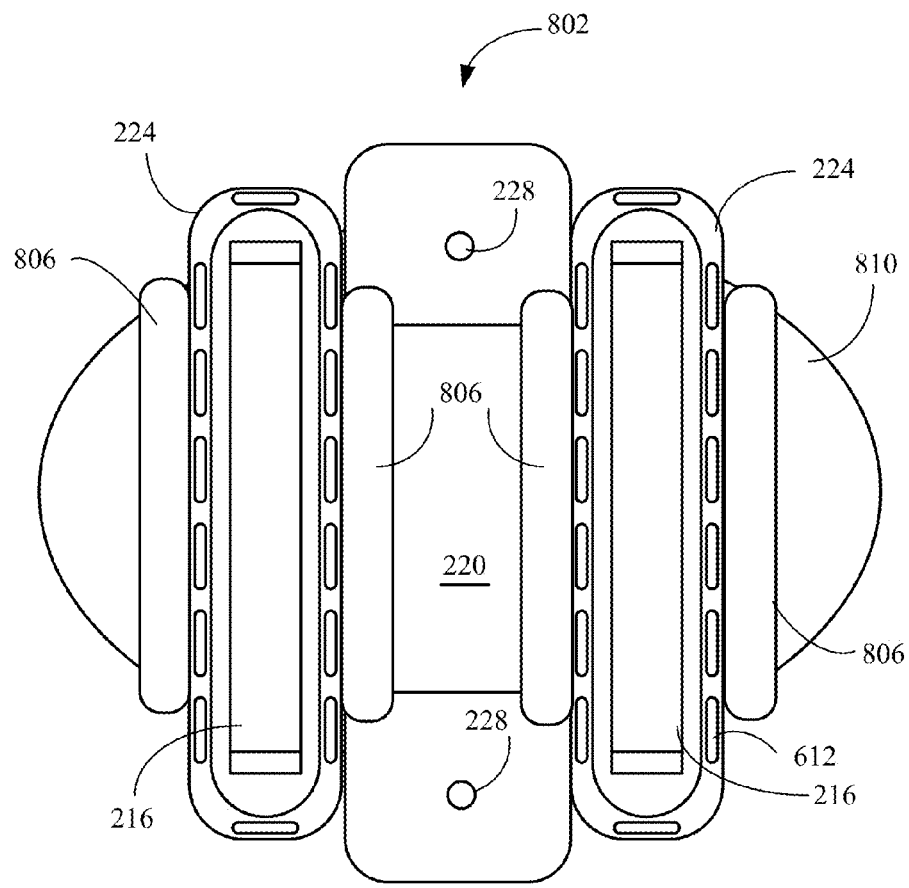
Figure 8E:
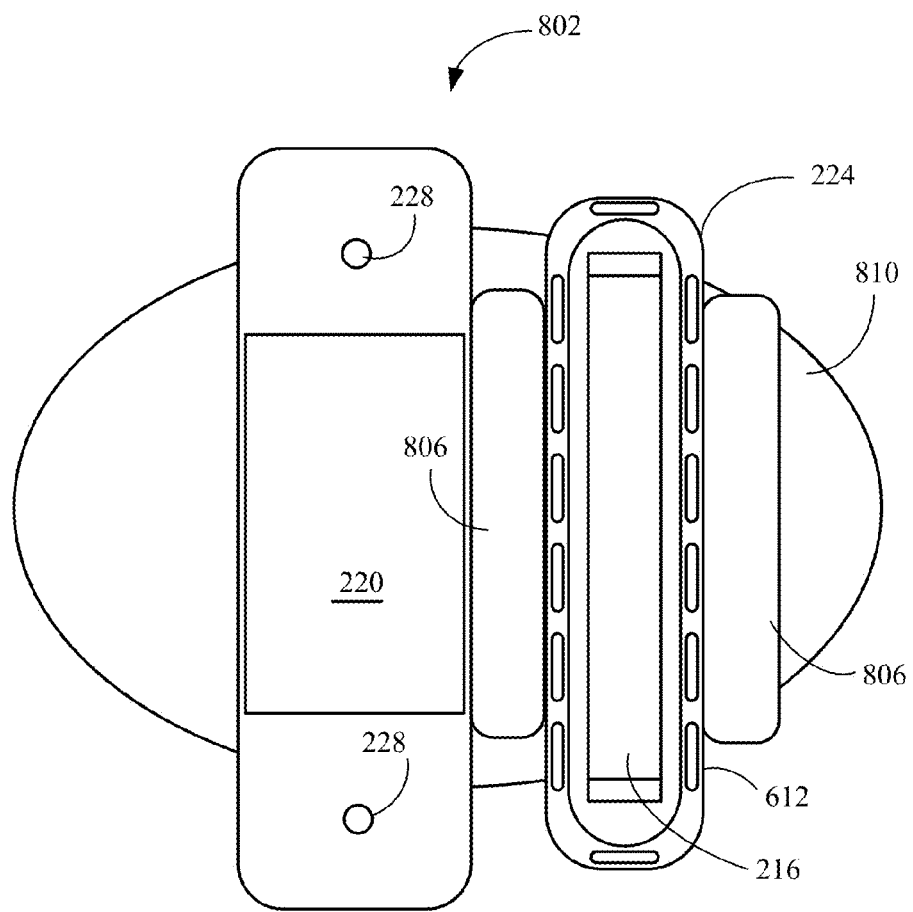

FIGS. 8A-8D illustrate variations in a third embodiment, with the figures being referred to collectively as FIG. 8. FIG. 8A depicts an additional embodiment in which the applicator 802 includes one or more RF electrodes 806 configured to contact the treated segment of skin and provide RF energy to the segment of skin 814 (FIG. 8B) located between electrodes 806, the RF energy is generated by an RF generator located in applicator casing 810 (FIG. 8A). Typically, the electrical and electronic circuits of applicator 802 include circuits that enable power to one or more illumination sources and RF sources. When RF electrodes 806 touch the subject skin (as illustrated in FIG. 8B), they provide a path for the current of the electrical and electronic circuits of applicator 802. An impedance sensing mechanism senses the impedance change from an infinite value to a measurable finite value and activates supply of RF energy having a magnitude sufficient to produce a desired skin or tissue treatment effect. RF induced current flows through tissue 818 as shown by lines 822 between electrodes 806 heating tissue volume schematically indicated by reference numeral 826. Thus, the use of an applicator is safer than mechanical switching, since little or no RF is emitted if there is no contact of RF electrodes 806 and the skin. The electrical response to the impedance changes is faster than mechanical switching and if one electrode loses contact with the skin, the RF emission is instantly switched-off (Generally, a very low level of RF power may continue to be emitted in order to be able to activate the illumination sources and RF energy when contact with the skin will be once again established.) Optionally, applicator 802 may have an ON-OFF switch to switch off applicator 802 completely. FIG. 8C is another schematic illustration of the third exemplary embodiment of the applicator. In this embodiment, RF electrodes 806 are located at the external side of the cartridges 224 and FIG. 8D illustrates an additional embodiment of the applicator, where RF electrodes 806 are located on both sides of the cartridges 224. FIG. 8E illustrates still a further embodiment of the applicator 802, where only one cartridge 224 is used with RF electrodes 806 located on both sides of the cartridge 224.

All earlier described applicator 104 (FIG. 2) components, such as a hair removal mechanism, illuminators and their functionality are mutatis mutandis applicable to applicator 802.

Figures 9A, 9B:
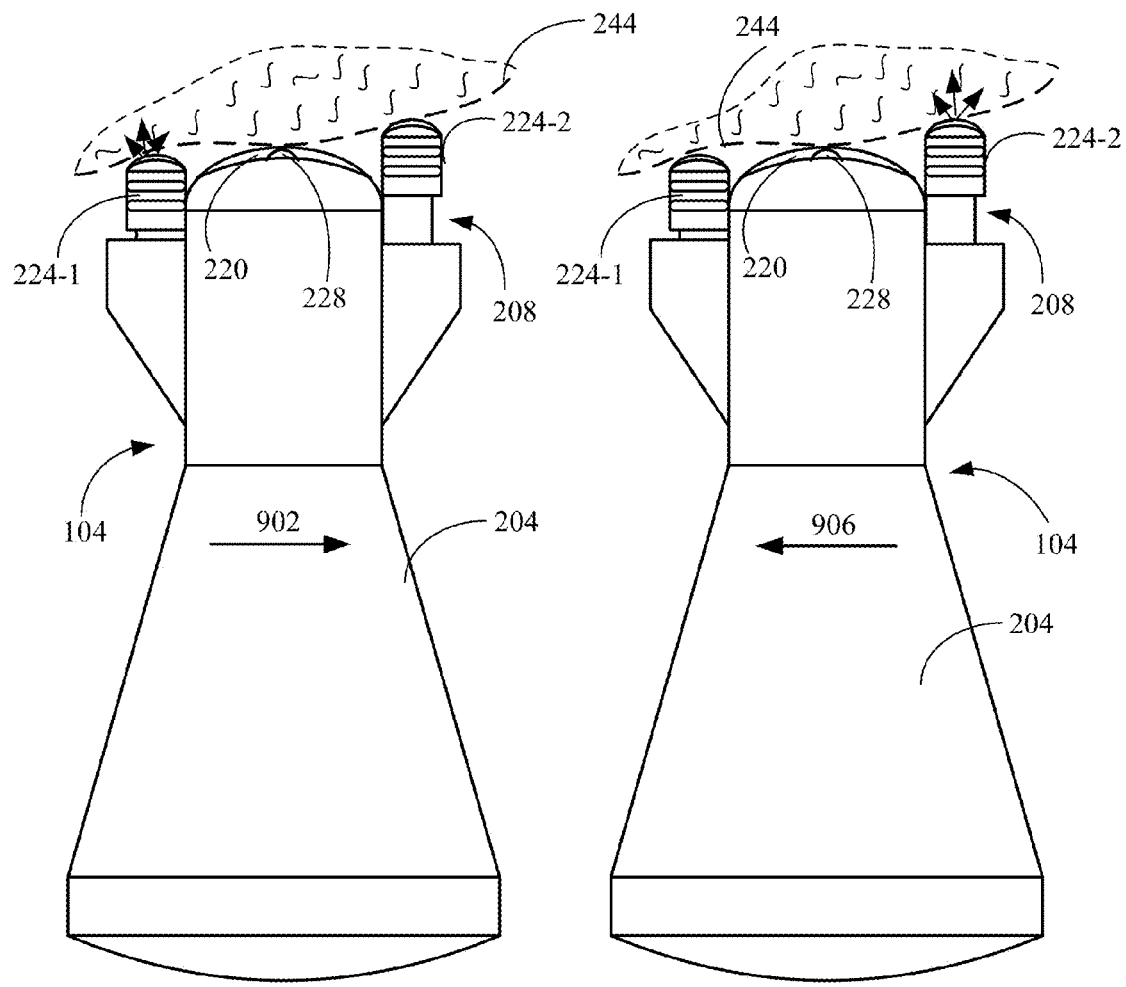
FIGS. 9A and 9B, collectively referred to as FIG. 9, are schematic illustrations of a hair removal treatment using the first exemplary embodiment of the present applicator.

FIGS. 9A and 9B, collectively referred to as FIG. 9, depicts a schematic illustration of a hair removal treatment using the first exemplary embodiment of the present applicator. The first end 208 of applicator 104 is applied to skin 244. This applies slight pressure on micro switches 228 and therefore hair removal mechanism 220 and appropriate illumination sources are enabled. (Generally, both the hair removal mechanism and the illumination source may be enabled by other mechanisms independent of a micro switch mechanism). The user of the applicator translates applicator 104 in a scanning motion in the first direction indicated by arrow 902 (FIG. 9A) from one segment of skin 244 to another skin segment. During the translation, hair removal mechanism 220 removes hair from the treated segment of skin 244. A motion direction sensor senses the movement direction and activates trailing illumination source located in cartridge 224-1 to illuminate a skin segment from which the hair was removed. Continuous illumination flux produced by the trailing illumination source 224-1 heats the skin segment from which earlier hair was attempted to be removed mechanically, weakens and perhaps destroys the hair follicles and bulbs. Typical useful values of the illumination flux would have a value in the range of 0.5 $J/cm^2$ to 20 $J/cm^2$. In addition to destroying hair follicles and bulbs, illumination flux accelerates skin-healing effect.

When applicator 104 moves in a second direction indicated by arrow 906 (FIG. 9B), hair removal mechanism 220 functions in a similar way and removes hair from the mechanically treated skin segment. The motion direction sensor senses the change in the movement direction and switches off the now leading illumination source, relative to the new movement direction, located in cartridge 224-1; the motion direction sensor then activates the illumination source located in cartridge 224-2, which has now become a trailing illumination source relative to the new movement direction, to illuminate a skin segment. Illumination sources located in cartridges 224-1 and 224-2 may operate simultaneously (concurrently) with hair removal mechanism 220. However, illumination sources located in cartridge 224-1 and 224-2 operate on different segments of skin 244 than the hair removal mechanism 220 operates. Illumination sources may operate in a continuous mode and their power set to cause a desired skin effect and prevent skin burns. An optional temperature sensor may be used to continuously measure skin temperature and accordingly deactivate the RF and/or light sources.

As noted the illumination flux produced by the trailing illumination source located in cartridge 224-1 generates the effects described above of stunning the hair shaft growth as well as skin-healing effect. The effect may be further enhanced by proper selection of the illuminating wavelength and intensity.

The trailing and leading illumination sources typically, may be operative to generate different flux values most appropriate for getting the desired effect. When illumination sources are LED based sources, such as shown in FIG. 7A, the trailing and leading illumination sources may be operative to emit different wavelengths more suitable for getting the desired effect. Generally, as previously explained, the illumination source cartridge may be constructed to include more than one lamp to operate them at different power levels or emit energy at different spectrums, as would be most appropriate for getting the desired treatment effect.

Figure 10:
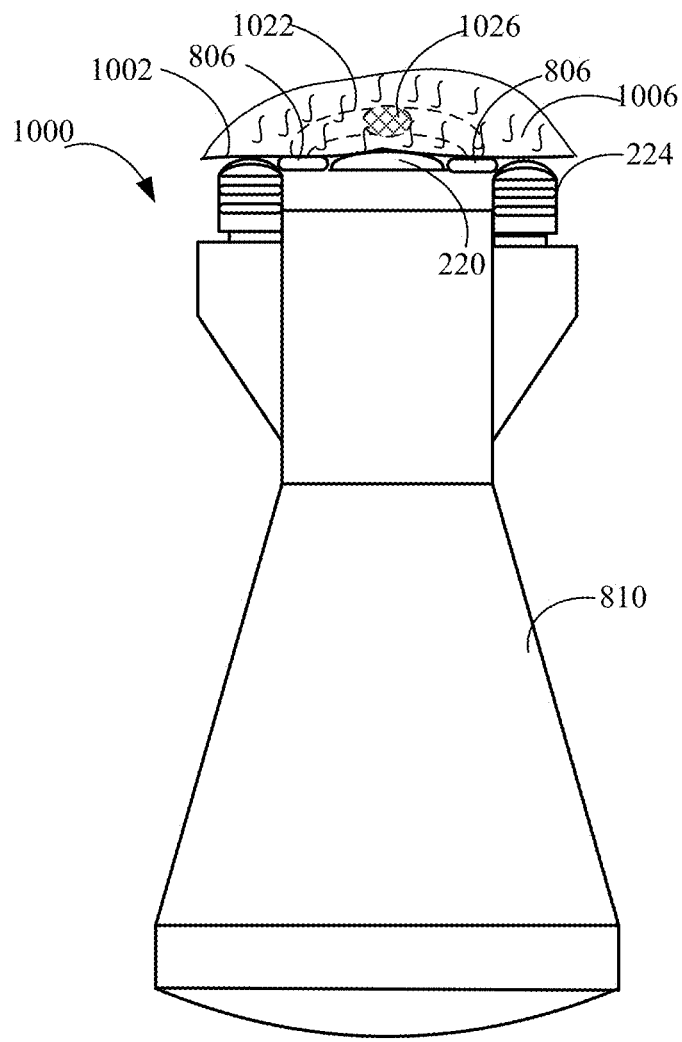
FIG. 10 is a schematic illustration of a hair removal treatment using the second exemplary embodiment of the present applicator.

FIG. 10 is a schematic illustration of a hair removal treatment using another exemplary embodiment of the present applicator. Applicator 1000 is applied to skin 1002 such that it forms a contact between RF electrodes 806 and skin 1002. Impedance sensing mechanism senses the change in the impedance from infinity to a certain value and activates electric and electronic circuits of applicator 1000. Thus, the impedance sensing mechanism can replace the micro switch mechanism described earlier, although both mechanisms may be combined to provide enhanced safety in the treatment. Mechanical hair removal mechanism physically removes the hair. RF induced current shown by lines 1022 heats tissue 1006 and in particular volume 1026, weakens or even destroys residual hair follicles and bulbs. The user of the applicator translates applicator 1000 in a scanning motion from one segment of skin 1002 to another skin segment and heats respective tissue volumes 1026. In the course of the translation, hair removal mechanism 220 removes hair from the segments of skin 1002 located over the heated tissue volumes. Motion direction sensor 232 (FIG. 2A) senses the movement direction and activates trailing illumination source 224 to illuminate a skin segment from which the hair was removed. Illumination flux produced by the trailing illumination source 224 weakens the hair follicle and hair shaft, and to some extent, heats the skin and destroys the remaining hair follicles and bulbs not removed by mechanical means. In addition to destroying hair follicles and bulbs, illumination flux accelerates skin-healing effect. All disclosed above illumination flux and wavelength variations and illumination source switching are mutatis mutandis applicable to the present embodiment that uses RF to heat deeper tissue layers.

Figure 11:
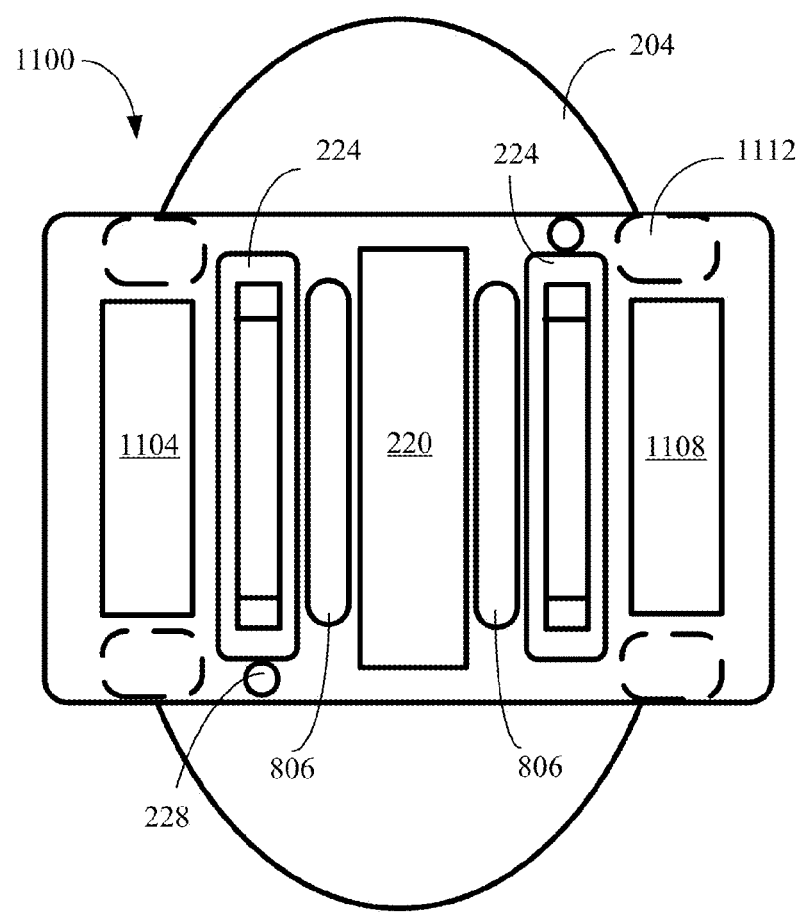
FIG. 11 is a schematic illustration of the forth exemplary embodiment of the present applicator.

The skin treatment results may be improved by proper preparation of the skin segment to be treated. Post treatment rash may be reduced by application of a solution, such as creams, lotions or other liquid or powder. FIG. 11 is a schematic illustration of the fourth exemplary embodiment of the present applicator. Applicator 1100, in addition to the earlier described hair removal mechanism 220, illumination sources 224, RF electrodes 806, and micro switches 228 includes a skin and hair pre-treatment device 1104 and a skin and hair post treatment device 1108. The skin and hair pre-treatment device 1104 may be operative to clean by spray or similar solution a segment of skin to be treated. The skin and hair post treatment device 1108 may be operative to disperse over the treated segment of the skin a cream or solution reducing irritation that the treatment may occasionally cause to the skin. Optional variable length spacers 1112 may be used to maintain a desired gap between the location of the hair removal mechanism and the skin.

Typically, any one of the applicators described will be electrically driven, i.e. by a drive rotating the hair removal mechanism and operating other units of the applicators. Alternatively, the applicator may be configured such that the sliding movement over the skin of the subject would provide a rotational movement to the hair removal mechanism.

Application of the method enables almost a hair free skin area to be achieved due to mechanical hair removal, and retard or completely eliminate hair re-growth enabled by (concurrent, or subsequent, or prior to mechanical hair removal) RF application and skin illumination Skin healing process is accelerated by selection of proper skin illumination wavelengths.

Figures 12A, 12B:
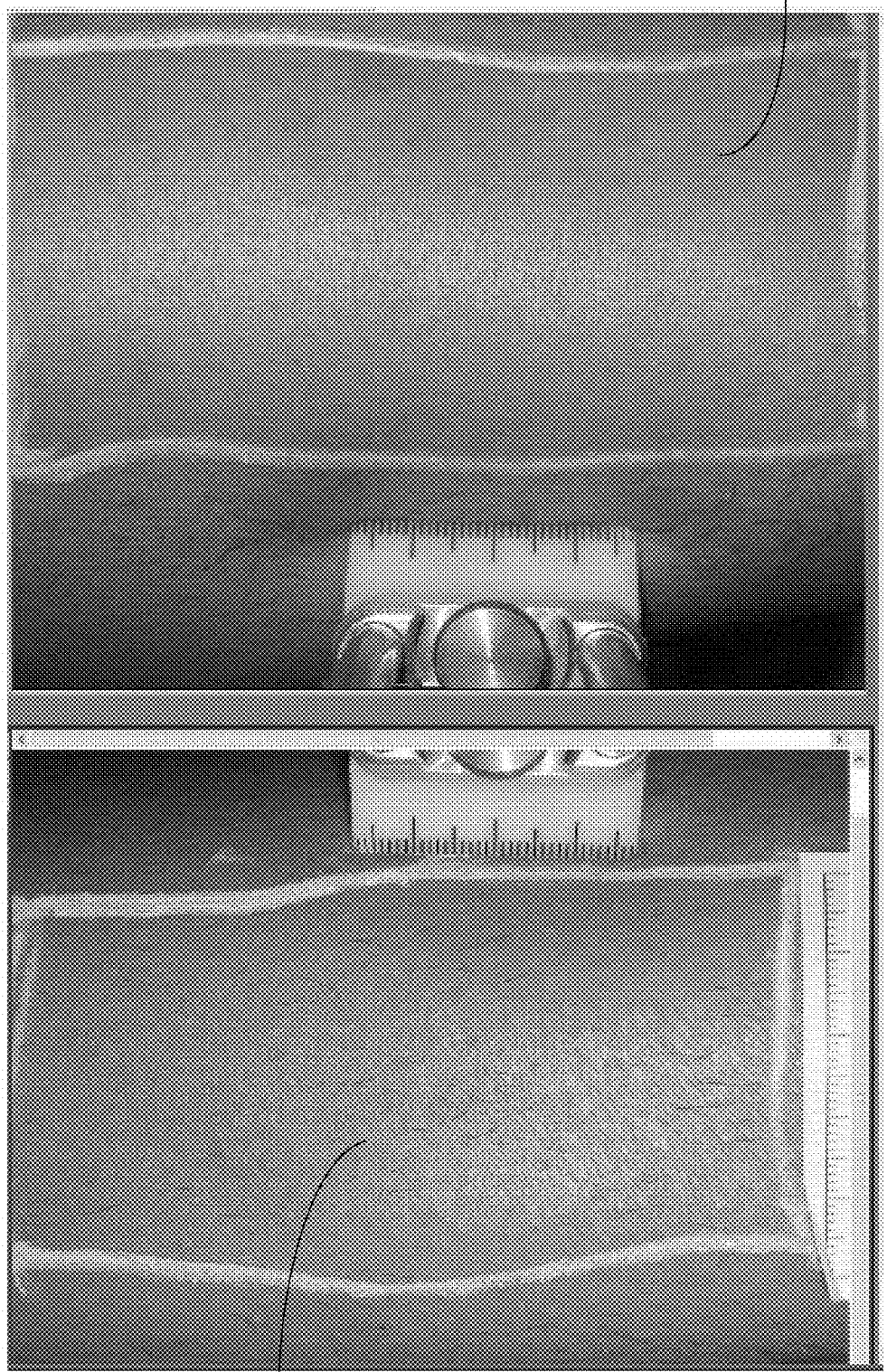
FIG. 12A and FIG. 12B, collectively referred to as FIG. 12, are photographic images of a segment of a subject skin treated by the present method and an image of a untreated segment (control segment) of a subject skin.

FIG. 12A and FIG. 12B, collectively referred to as FIG. 12, are photographic images of a segment of a subject skin treated by the present method (FIG. 12B) and an image of non-treated segment (control) of a subject skin (FIG. 12A). The treated segment 1206 does not contain even residual hair. The non-treated segment 1202 is shown for comparative purposes.

Several embodiments have been described using detailed descriptions thereof that are provided by way of example and are not intended to be limiting. The described embodiments comprise different features, not all of which are required in all embodiments. Some embodiments utilize only some of the features or possible combinations of the features. Variations of embodiments that are described and embodiments comprising different combinations of features noted in the described embodiments will occur to persons of the art.

It will be appreciated by persons skilled in the art that the follow claims are thus not limited to the disclosed embodiments, features, functions, etc. but that rather the claims may encompass additional embodiments.

What is claimed is:

1. A method for treating a skin segment for the removal of hair from the skin segment, wherein the skin segment has a particular contour, said method comprising:
    applying to skin an applicator having an exchangeable hair removal mechanism located between two detachable illumination cartridges, the detachable illumination cartridges being detachable from an applicator casing and configured to follow the contour of the skin segment being treated, a pair of RF electrodes configured to heat the skin segment, and an impedance sensing mechanism;
    sensing change in the impedance of the skin segment between the pair of RF electrodes and activating electric and electronic circuits of the applicator;
    translating the applicator in a scanning motion from one location of the skin segment to another location of the skin segment;
    applying the exchangeable hair removal mechanism to hair within the skin segment to remove the hair; and
    applying RF energy to the skin segment to heat tissue of the skin segment, thereby weakening and destroying residual hair follicles and hair shafts;
    wherein applying the exchangeable hair removal mechanism to remove hair comprises pulling at least one hair shaft and an area of skin surrounding the at least one hair shaft to form a goose bump like protrusion and goose bump like peak; and
    cutting the at least one hair shaft substantially close to the goose bump like peak; and
    wherein at least one motion sensor is operative to: activate at least one illumination source according to the applicator displacement direction, and de-activate at least one of the illumination cartridges according to the applicator displacement direction such that a trailing illumination cartridge is activated relative to the applicator displacement direction.

2. A treatment method of a skin segment to effectuate hair removal, said method comprising:
    applying to the skin an exchangeable mechanical hair removal mechanism located between two detachable illumination cartridges, the illumination cartridges being detachable from an applicator casing and configured to follow the contour of a surface of a skin segment to be treated, wherein the presence of finite impendence sensed between RF electrodes activates:
    the application of RF energy to the skin segment to heat the skin segment; and illuminating the skin segment with at least one detachable illumination cartridge; and wherein
    the exchangeable mechanical hair removal mechanism a) pulls at least one hair shaft and skin surrounding the at least one hair shaft to form a goose bump like protrusion having a goose bump like peak and b) cuts the at least one hair shaft substantially close to the goose bump like peak;
    and wherein a comb type protective plate positioned between the exchangeable mechanical hair removal mechanism and the goose bump like protrusion protects the goose bump like protrusion and surrounding skin from damage by the exchangeable mechanical hair removal mechanism and wherein at least one motion sensor is operative to activate one of the illumination cartridges and de-activate the other illumination cartridge according to the applicator displacement direction.

* * * * *